United States Patent [19]
Sandler et al.

[11] Patent Number: 6,056,703
[45] Date of Patent: *May 2, 2000

[54] METHOD AND APPARATUS FOR CHARACTERIZING GASTROINTESTINAL SOUNDS

[75] Inventors: Richard H. Sandler, Evanston; Hussein A. Mansy, Chicago, both of Ill.

[73] Assignee: Rush Presbyterian-St Luke's Medical Center, Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/717,184

[22] Filed: Sep. 20, 1996

Related U.S. Application Data

[63] Continuation-in-part of application No. 08/649,081, May 17, 1996, abandoned, which is a continuation-in-part of application No. 08/627,309, Apr. 3, 1996, abandoned.

[51] Int. Cl.[7] .................................................. A61B 5/103
[52] U.S. Cl. ............................................ 600/593; 600/595
[58] Field of Search .................................... 128/773, 774, 128/633, 775, 715; 600/593, 586, 587

[56] References Cited

U.S. PATENT DOCUMENTS

| | | | |
|---|---|---|---|
| 4,792,145 | 12/1988 | Eisenberg et al. | 128/715 |
| 4,823,808 | 4/1989 | Clegg et al. | 128/773 |
| 4,823,809 | 4/1989 | Clegg et al. | 128/773 |
| 4,991,581 | 2/1991 | Andries | 128/715 |
| 5,010,889 | 4/1991 | Bredesen et al. | 600/586 |
| 5,140,994 | 8/1992 | Campbell et al. | 128/782 |
| 5,165,417 | 11/1992 | Murphy, Jr. | 128/716 |
| 5,301,679 | 4/1994 | Taylor | 128/773 |
| 5,435,317 | 7/1995 | McMahon et al. | 128/716 |
| 5,438,985 | 8/1995 | Essen-Moller | 128/633 |

OTHER PUBLICATIONS

Dalle, D. and Devroede, G., "Computer Analysis of Bowel Sounds," *Computers in Biology and Medicine*, Feb. 1975 4 (3–4) pp. 247–254.

Sugrue et al., "Computerized Phonoenterography: The Clinical Investigation of a New System," *Journal of Clinical Gastroenterology*, vol. 18, No. 2, 1994, pp. 139–144.

Poynard, et al., "Qu'attendre des systemes expert pour le diagnostic des troubles fonctionnels intestinaux," *Gastroenterology Clinical Biology*, 1990, pp. 45C–48C.

Cullen, P.T., Storey, B.E., Cuschieri, A. and Campbell, F.C., "Detection of Clustered Gastrointestinal Contractions in Partial Intestinal Obstruction by Surface Vibration Anaysis, "vol. 210, No. 2, *Ann. Surg.* pp. 234–238, Aug. 1989.

Yoshino, H., Abe, Y., Yoshino, T., Ohsato, K., "Clinical Application of Spectral Analysis of Bowel Sounds in Intestinal Obstruction," *Dis. Col. & Rect..* pp. 753–757, vol. 33, No. 2, Sep. 1990.

Garner, C.G. and Ehrenreich, H., "Non–invasive Topographic Analysis of Intestinal Activity in Man on the Basis of Acustic [sic] Phenomena", *Res. Exp. Med.*, vol. 189, pp. 129–140, 1989.

Politzer, J.D., Devroede, G., Vasseur, C., Gerard, J. and Thibault, R., *Gastroenterology*, vol. 71, No. 2, pp. 282–285, 1976.

(List continued on next page.)

*Primary Examiner*—Cary O'Connor
*Assistant Examiner*—Pamela L. Wingood
*Attorney, Agent, or Firm*—Fitch, Even, Tabin & Flannery

[57] ABSTRACT

A method and apparatus for characterizing gastrointestinal sounds includes a microphone array to be positioned on a body for producing gastrointestinal sound signals. The signals are digitized and their spectra and duration is determined by a processor. A characterization as to the state of the gastrointestinal tract is made on the basis of the spectra and duration of the sound or event.

3 Claims, 37 Drawing Sheets

OTHER PUBLICATIONS

Arnbjornsson, E. and Bengmark, S., Auscultation of Bowel Sounds in Patients with Suspected Acute Appendicitus–an Aid in the Diagnosis?, *Eur. Surg. Res.*, vol. 15, pp. 24–27 (1983).

Farrar, J. and Ingelfinger, F., "Gastrointestinal Motility As Revealed By Study of Abdominal Sounds," 56th Annual Meeting of the American Gastroenterological Association, Atlantic City, NJ, Jun. 1995, pp. 789–803.

Watson, W. and Knox, E., "Phonoenterography: the recording and analysis of bowel sounds," vol. 8, pp. 88–94 (1967).

Arnbjornsson, E., "Normal and Pathological Bowel Sound Patterns," Annales Chirurgiae et Gynaecologiae, vol. 75, pp. 314–318 (1986).

Barclay, G., Solomon, A. and Wade, M., "Apparatus to Record Bowel Sounds and Intestinal Pressures," Proceedings of the Physiological Society, Nov. 4–5, 1996, pp. 5–6.

Politzer, J.D., Devroede, G., Vasseur, C., Gerard, J. and Thibault, R., "The Genesis of Bowel Sounds: Influence of Viscus and Gastrointestinal Content, " *Gastroenterology*, vol. 71, No. 2 pp. 282–285, 1976.

Baker, J.A., Humphrey, S.J.E., and Wolff, H.S., Socially Acceptable Monitoring Instruments (SAMI), Proceedings of the Physiological Society, pp. 4P–5D, 405 Nov. 1966.

U.S. application No. 08/627,309, Sandler et al., filed Apr. 3, 1996, for Method and Apparatus for Characterizing Gastrointestinal Sounds.

U.S. applicaton No. 08/649,081, Sandler et al., filed May 17, 1996, for Method and Apparatus for Characterizing Gastrointestinal Sounds.

U.S. application No. 08/970,026, Sandler et al., filed Nov. 13, 1997, for Method and Apparatus for Characterizing Gastrointestinal Sounds.

International application No. PCT/US/05239, filed Mar. 31, 1997 by Rush–Presbyterian—St. Luke's Medical Center for Method and Apparatus for Characterizing Gastrointestinal Sounds claims priority from three of the four Sandler applications: U.S. application Nos. 08/627,309, 08/649,081, and 08/717,184.

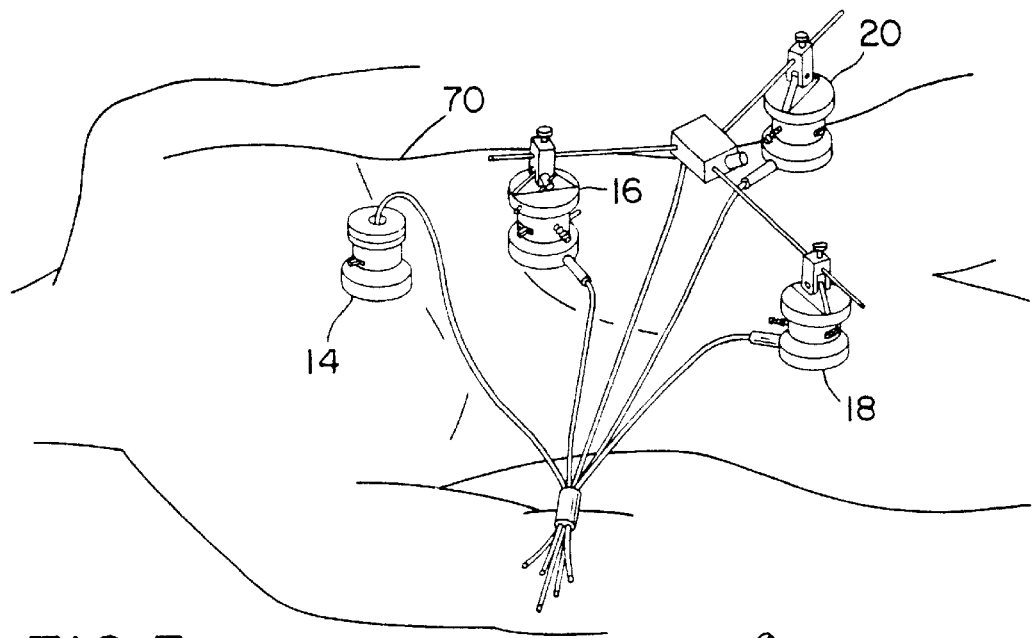
FIG. 3
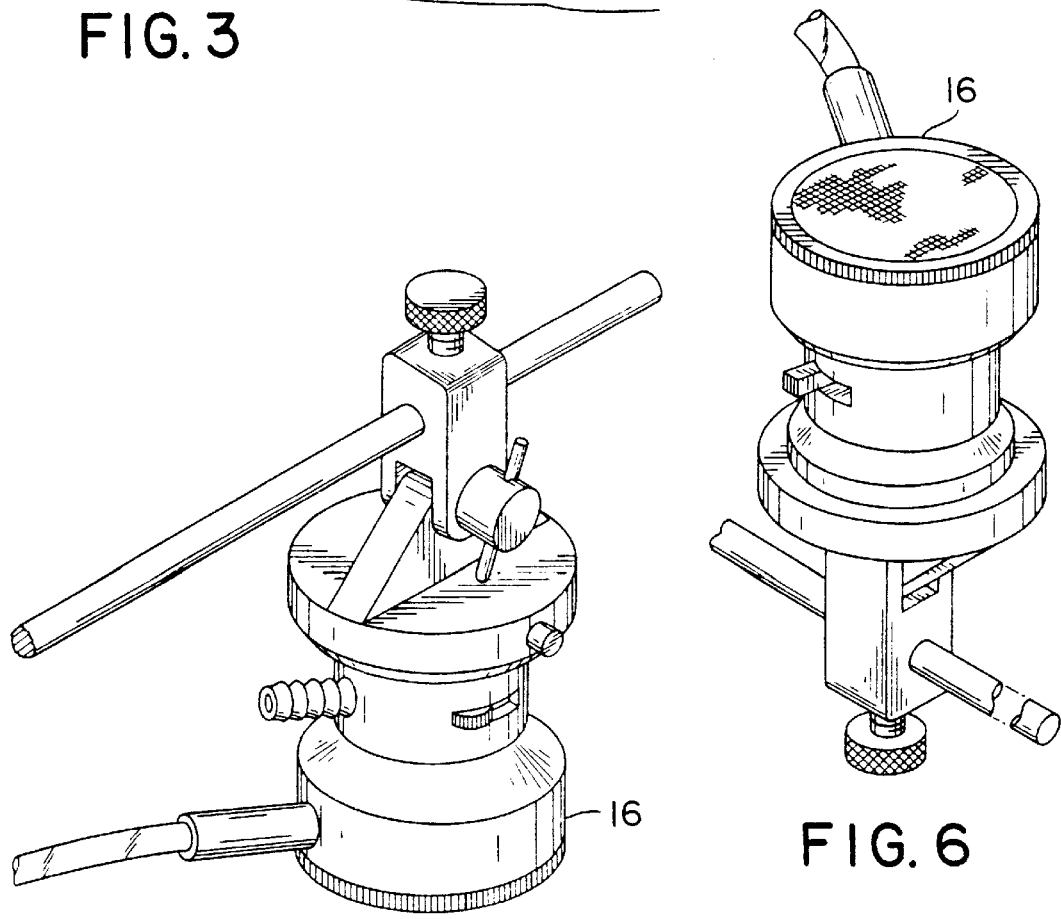
FIG. 5
FIG. 6

METHOD AND APPARATUS FOR CHARACTERIZING GASTROINTESTINAL SOUNDS

CROSS REFERENCE TO RELATED APPLICATIONS

This is a continuation-in-part of copending U.S. application Ser. No. 08/649,081, filed May 17, 1996, now abandoned which is a continuation-in-part of copending U.S. application Ser. No. 08/627,309, filed Apr. 3, 1996 now abandoned.

BACKGROUND OF THE INVENTION

The invention relates in general to a method and apparatus for characterizing gastrointestinal sounds and in particular to a method and apparatus employing a microphone array attachable to a patient's body for collecting sounds from multiple sources in the body and a computer system for receiving digitized gastrointestinal sound signals and determining the spectra and duration of the sounds and characterizing states of the gastrointestinal tract on the basis of the spectrum and duration.

It has been known in the past to employ electronic analysis of sounds from the gastrointestinal tract as an adjunct to the physician auscultating the gastrointestinal tract in an attempt to determine quickly and with a minimum of diagnostic equipment the condition of the patient. In the past, for instance, as disclosed in U.S. Pat. No. 5,301,679, a method and system was provided for providing diagnostic information for various diseases including diseases of the gastrointestinal tract by capturing body sounds in a microphone placed on the body surface or inserted orally or rectally into the gastrointestinal tract. The spectrum analyzer used a real time audio one-third octave technique using a plurality of analog filters and a peak detector provide a log calculation of envelope amplitudes. Other systems also used microphones sensitive to specific frequency ranges and are exemplified by Dalle, et al. "Computer Analysis In Bowel Sounds," *Computers in Biology and Medicine* February 1975 4(3–4) pp. 247–254; Sugrue et al. , "Computerized Phonoenterography: The Clinical Investigation of the New System," *Journal of Clinical Gastroenterology*, Vol. 18, No. 2, 1994, pp. 139–144; Poynard, et al., "Qu'attendre des systemes experts pour le diagnostic des troubles fonctionnes intestinaux," *Gastroenterology Clinical Biology*, 1990, pp. 45C–48C. Also of interest are U.S. Pat. Nos. 1,165,417; 5,010,889; 4,991,581; 4,792,145. Unfortunately, none of the systems relate to using specific morphological filtering an event characterization of the type which might be able to identify ileus or small bowel obstruction or the like. The prior systems seem to have suffered from the inability to cope with relatively irregular sounds and irregular signals and to pick events of detail from the signal. Many of the systems used averaging techniques on the raw signal, which would tend to obscure the event of interest in noise or other unwanted portions of the signal and thus actually work against the diagnostician attempting to characterize genuine gastrointestinal sounds as opposed to other sounds coming form the body. Thus, it would appear that despite the use of sophisticated spectral techniques and the like the prior art, having been unable to identify events, appeared to operate on relatively noisy data from which it would be difficult to extract meaningful conclusions. Accordingly, what is needed is a system which can quickly and easily identify such conditions.

SUMMARY OF THE INVENTION

The invention is directed to a method and apparatus including a microphone array including three microphones fixed on a mount for precise positioning with respect to key location of the anatomy of the patient with a fourth free microphone which may be placed adjacent to the sternum of the patient for picking up breathing, cardiac and environmental sounds and the like which are to be subtracted from the gastrointestinal sounds and are treated as noise. The microphones feed a sound equalizing system for selection of certain sound frequency ranges which in turn feeds analog sound signals representative of gastrointestinal sounds to a tape recorder. The tape recorder is connectable to a computer which includes an analog to digital converter. Digitized multiple gastrointestinal sounds may then be processed by a computer in accordance with morphological filtering algorithms which characterize both the spectra and the duration of the sounds emanating from the gastrointestinal tract. In addition, the computer can subtract out components of sounds related to the background noise from the surrounding room or from the breathing which is picked up by a free microphone. An output indication may be provided to the physician or other health care worker through a printer or a video display screen which provides an indication as to the type of sound and a characterization in some cases as to the condition of the patient such as ileus and the like.

The present system is particularly characterized by the fact that the initial processing of the digitized audio signals relates to selecting gastrointestinal events of interest from extended noisy audio signals. One way in which this has been done in the present application is to use an amplitude thresholding system to look for events of interest and then to focus additional processing on those events. This approach does not appear to have been taken in the previous systems and may have reduced their ability to extract meaningful data from the relatively noisy environments in which they operate.

It is a principal aspect of the present invention to provide a gastrointestinal sound processing system which can characterize individual gastrointestinal events on diagnostic basis.

It is another aspect of the present invention for providing a gastrointestinal sound characterization system which intercepts sounds from multiple locations in the human body for diagnostic purposes.

Other aspects of the present invention will be apparent to one of ordinary skill in the art upon a perusal of the following specification and claims in light of the accompanying drawings.

BRIEF DESCRIPTION OF THE DRAWINGS

FIG. 3 is a perspective view of a portion of a human torso showing the location of multiple microphones on the torso for picking up gastrointestinal sounds and background noise;

FIGS. 5 and 6 are upright and upside down perspective views of one of the microphones of the array;

DETAILED DESCRIPTION OF THE PREFERRED EMBODIMENTS

Figure 1:
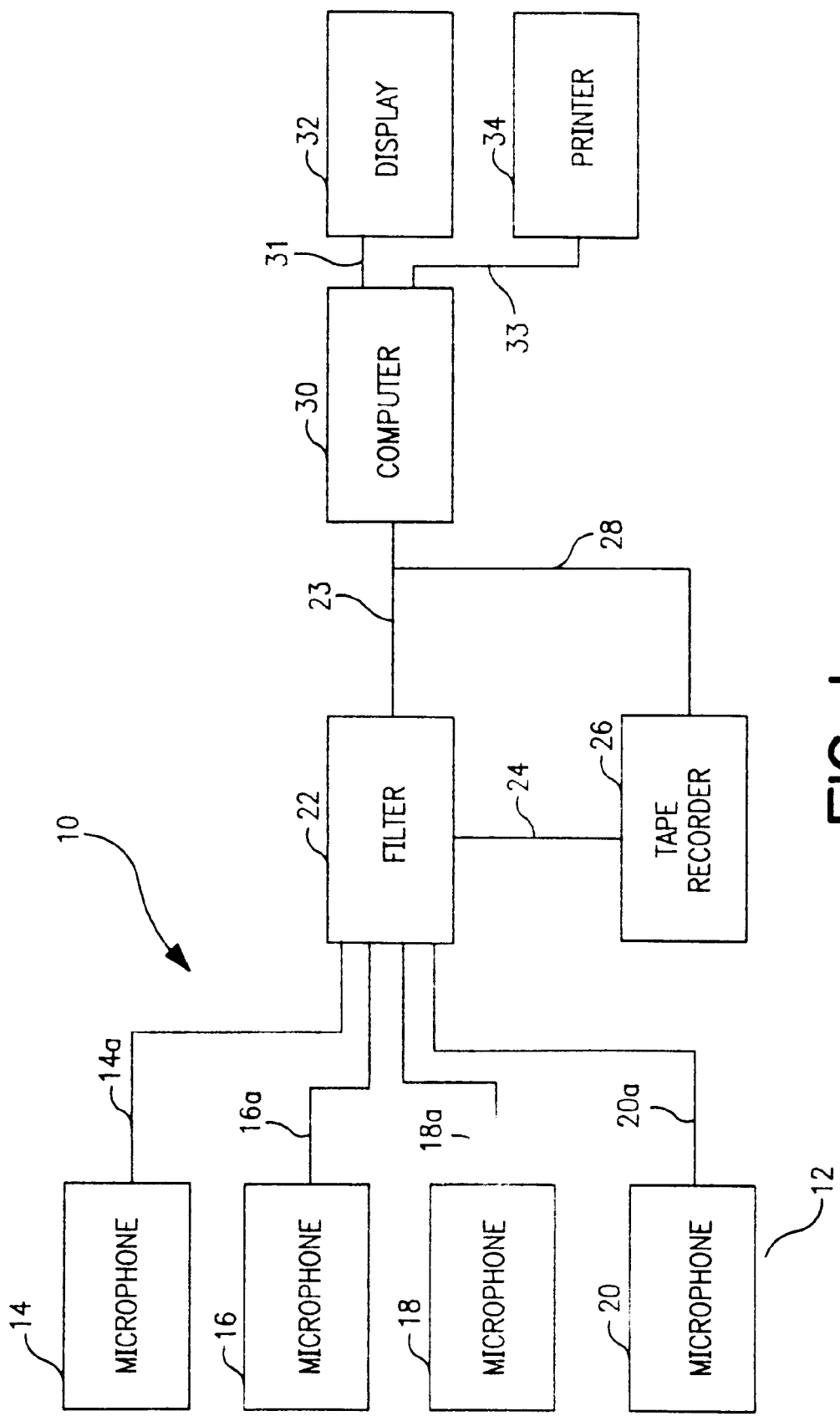
FIG. 1 is a block diagram of an apparatus embodying the present invention for gastrointestinal sound processing.

Referring now to the drawings and especially to FIG. 1, an apparatus for characterizing gastrointestinal sound is generally shown therein and identified by numeral 10. The apparatus 10 includes a microphone array 12 having a free microphone 14, an array microphone 16, a second array microphone 18 and a third array microphone 20 coupled to filter and amplifier 22 which feeds multiple analog signals representative of the gastrointestinal sounds over leads 24 to a Tascam 2000 multichannel tape recorder 26 where the analog signals may be recorded in analog format. The sound signals may then be transferred over lead 28 to a computer 30 for analysis Following analysis output results may be displayed on a video display terminal 32 or output through a printer 34.

Figure 2:
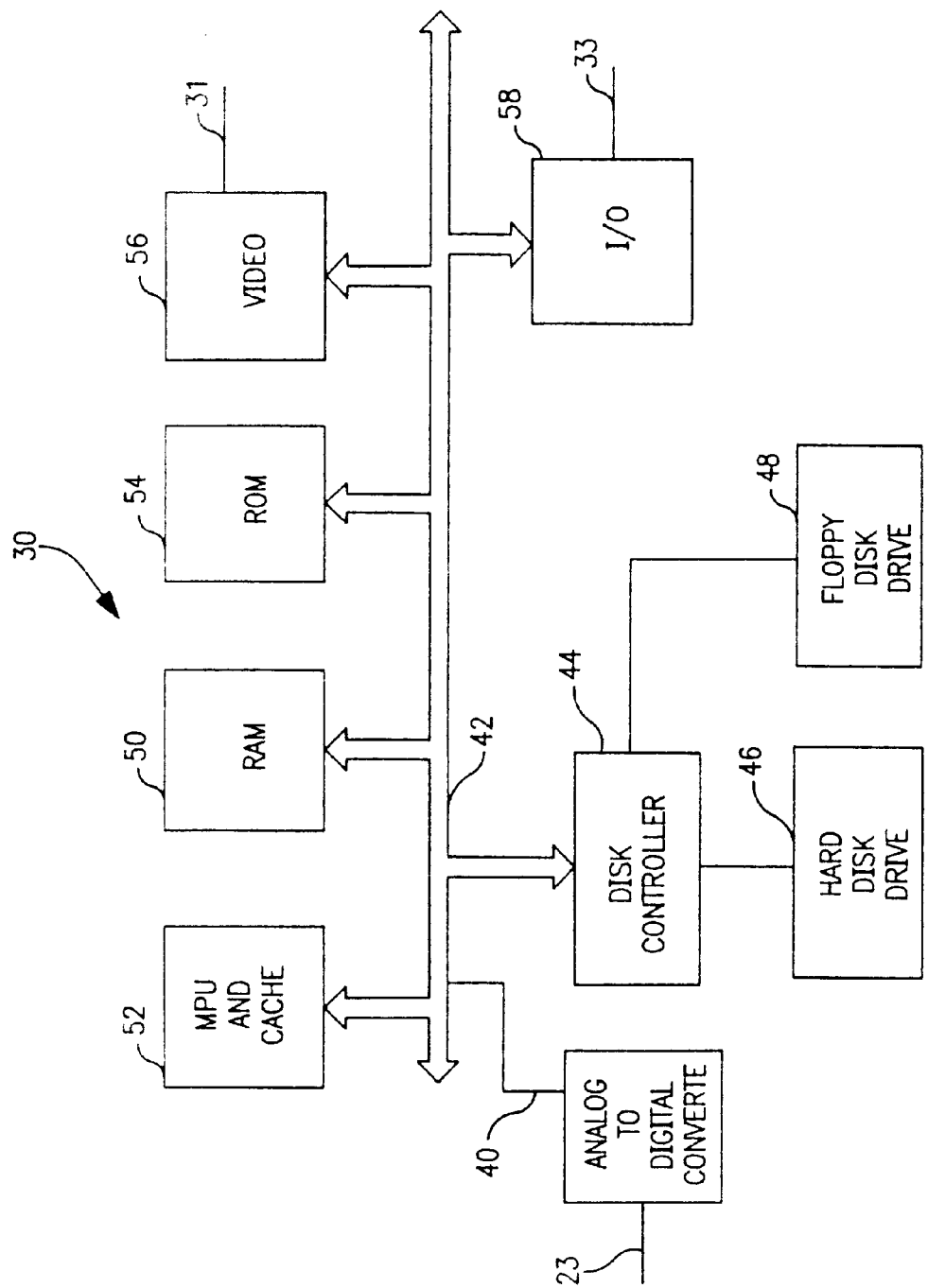
FIG. 2 is a block diagram of a computer and associated hardware shown in FIG. 1.
Figure 4:
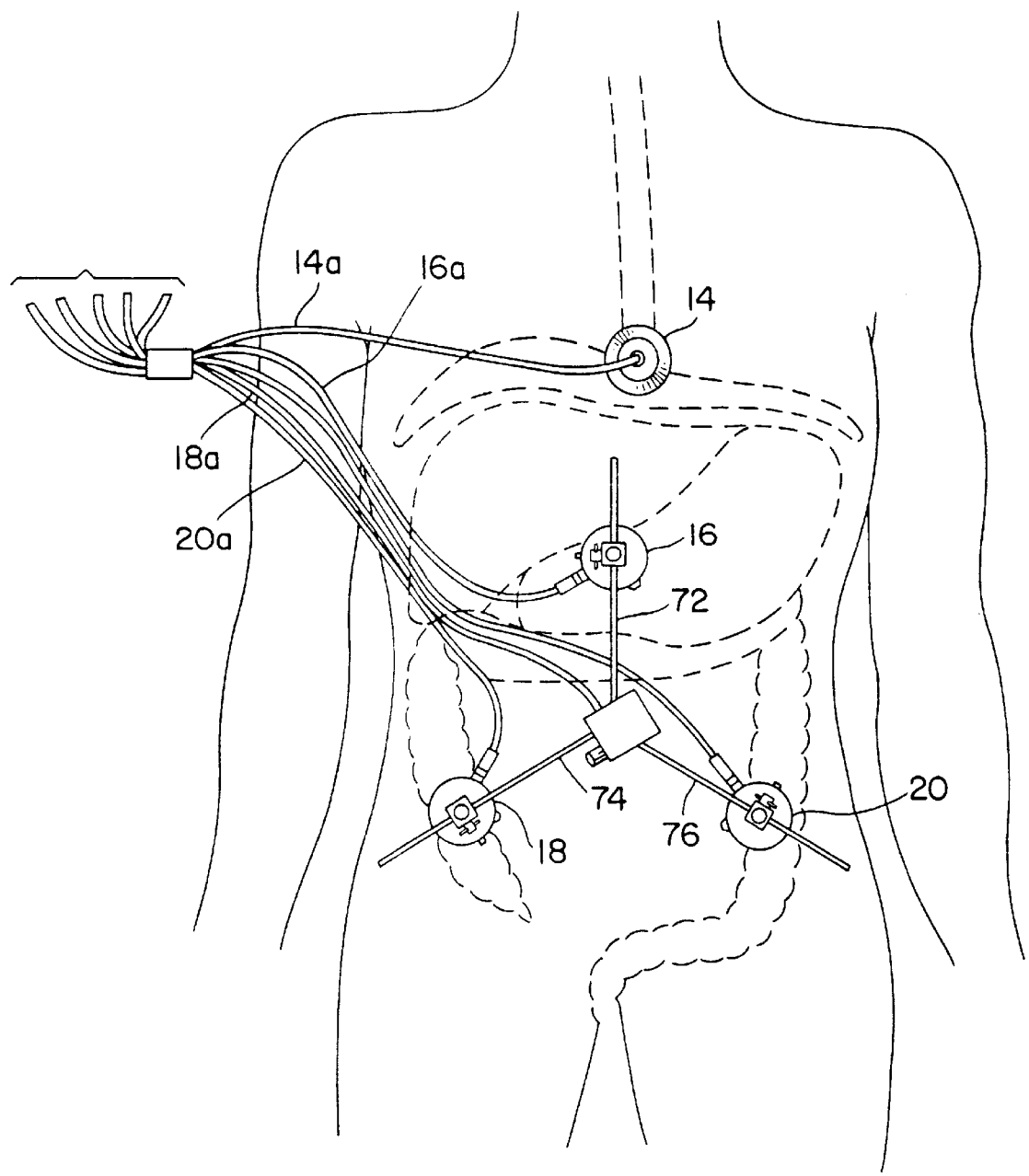
FIG. 4 is an elevational view showing portions of the interior organs of the body in dotted form showing the arrangement of the microphone array on the body.

Referring now to FIG. 2, a block diagram of the computer 30 is shown therein. The computer 30 receives the analog gastrointestinal sound signals on a line 23 at an analog to digital converter. The gastrointestinal signals are digitized and fed over lines 40 to a system bus 42 of the computer 30. The computer 30 includes a disk controller 44 having connected to it a hard disk drive 46 and a floppy disk drive 48. The hard disk drive 46 stores a program as represented by the flow charts of FIGS. 7 through 37 inclusive. Upon receipt of sound signals from a patient the software routines are transferred from the hard disk drive 46 through the disk controller 44 to the system bus 42 and are loaded into random access memory 50 connected to the system bus for execution by a microprocessor 52. Portions of the code and data of the software may be stored from time to time in a cache memory associated with the microprocessor 52. Read only memory 54 contains operating system information and outputs may be provided from the system bus by a video controller 56 to a video output line 31 connected to the display 32. Likewise, outputs may be connected through an input/output module, having parallel and serial ports 58, through a line 33. The microphone array 12, as may best be seen in FIGS. 3 and 4, microphones 14 through 20 placed on a torso 70 of a human being with the free microphone 14 being placed near the sternum and the array microphones 15 through 20 attached slidingly to array arms 72, 74 and 76. The sliding adjustable microphone harness is necessary to accommodate subjects of a wide variety of sizes. The microphones respectively are located to pick up multiple gastrointestinal sound sources from the human torso to provide analog signals to the computer 30.

The computer 30, by execution of the routines shown in FIGS. 7 through 43, inclusive, determines the spectra and the duration of the individual gastrointestinal events and provides an output indication thereof in response to the signal and the variables input as set forth in the tables below. The use of the multiple microphone array in combination with the routines set forth in the flow charts which are executed by computer allows quick and easy analysis of the gastrointestinal sounds for the determination of conditions such as small bowel obstruction, ileus and the like.

Figure 7:
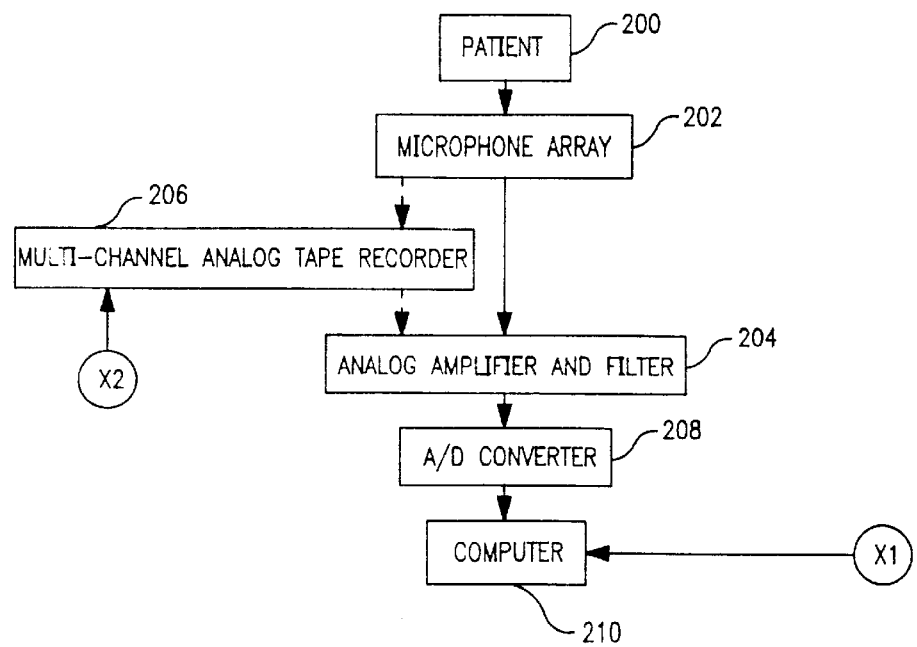
FIG. 7 is a flow diagram of a system for collecting and processing gastrointestinal sounds.

Referring now to the drawings and especially to FIG. 7, an overall flow diagram for gastrointestinal sound capture is shown herein wherein in a first step a patient 200 is fitted with the microphone array in a step 202 following which sounds captured by the microphone array 202 are fed to an analog amplifier and filter. Prior to analyzing captured sound the variable set found in Table 2 are in initialized to proper values. Table 2 provides optimized values of these settings for the current hardware and system.

TABLE 1

| ABBREVIATIONS | |
|---|---|
| $AMP^S$ | Amplitude of structuring elements |
| BNDFLT | Name of band-pass filter array of coefficients |
| chr_mx | Maximum coherence value |
| cntr | Dummy counter variable |
| d_c | Duration of current event |
| dd1, dd2, dd3 | Duration of detected events in other channels |
| DIST_CLASS | Average distance between subjects in the same class excluding current subject |
| DIST_SUBJ | Average distance between current subject and other members in the same class |
| dly1, dly2, dly3 | Interchannel delay, in seconds |
| $DT\_LN^S$ | length of data processing array |
| DT_RD | Number of data points to read from file |
| dn | Number of elements |
| DT_PTS | Number of data points in file |
| DTRD | Number of data points to read |
| dr1, dr2, dr3 | Duration of related events in other channels |
| dur | Event duration |
| DUR_MED | Median duration for all events |
| ed, ed1, ed2, ed3 | End times of detected events |
| ENPARR | Name of envelop array |
| ENPMAX | Envelope value at the envelop histogram maximum |
| ENPPOS | Envelop value when histogram slope first becomes positive |
| env_val | A point of the digital envelope data |
| er, er1, er2, er3 | End times of the related event |
| ev_ch | Channel of current event |
| EV_RATE | The average event rate during the recording time |
| EV_TSR | Event time series |
| f_dom | Dominant frequency of an event |
| F_DOM_MED | The median dominant frequency of all events |
| $FH^S$ | Value of the higher frequency (for low-pass filter) |
| $FL^S$ | Value of the lower frequency (for high-pass filter) |
| FL_SZ | Data file size in bytes |
| $FO^S$ | Filter order |
| $FS^S$ | Sampling frequency |
| G | The filtered signal |
| H | Filter coefficients |

TABLE 1-continued

| ABBREVIATIONS | |
|---|---|
| HLBFLT | Name of Hilbert filter array of coefficients |
| HMIN_D | Delay value corresponding to the minimum in the histogram of interchannel delay |
| HSTENP | Name of envelope histogram array |
| HSTMAX | Maximum value of histogram |
| HSTSLOP | Name of histogram slope array |
| i | Dummy variable |
| ich_dly | Interchannel event delay |
| ICH_TH | Interchannel event delay threshold |
| i_dur | Index of event duration |
| i_n | Index for the noise data array |
| i_p | Index for the primary data array |
| i_strt | Index of event start (equals the start of event start in number of points) |
| j | The square root of (−1) |
| $K^S$ | Number of nearest neighbors |
| mxlc | Location of the maximum |
| mxlc_r | Location of the maximum of correlation |
| mxlc_h | Location of the maximum of coherence |
| $MU^S$ | The adaptation parameter |
| N_EV | Total number of events in the whole the recording |
| nf | The filter noise data element |
| N_MIC | Number of microphones |
| n_rt | Number of related events |
| nxcr_mx | Maximum of normalized cross correlation |
| $OVLAP^S$ | Number of overlap points |
| P | Primary input channel data array |
| REC_RUR | The recording duration |
| rt_strt | Related event start time, in seconds |
| rt_pp | Peak to peak amplitude of related event, in volts |
| sdev | Deviation of event spectral morphology from that of known vascular sounds |
| SMOARR | Name of smoothed envelop array |
| spcg | Event spacing |
| $SPCG\_TH^S$ | Event spacing threshold for pasting events |
| STR_ELE | Name of structuring elements array |
| SUBJ_CLASS_RATIO | Ratio of subject/class distance |
| SUPARR | Name of supplementary array |
| tr1, tr2, tr3 | Start time of related events in other channels |
| td1, td2, td3 | Start time of detected events in other channels |
| t_c | Start time of current event |
| t_dur | Event duration, in seconds |
| t_dur_n | Duration of the newer event, in seconds |
| t_strt | Event start time, in seconds |
| t_strt_n | Start time of newer event, in seconds |
| tn_amp | Amplitude of the nearest event |
| tn_dur | Duration of the nearest events, in seconds |
| tn_strt | Start time of near events, in seconds |
| td | Start time of detected events |
| tr | Start time of the related events |
| x | A complex signal |

TABLE 2

SETTINGS

| NAME | DESCRIPTION | DEFAULT VALUE | RANGE |
|---|---|---|---|
| $AMP^S$ | Amplitude of structuring elements | 0 | 0–2 |
| $AUT\_TH^S$ | Turning the auto threshold on and off | 0 | 0,1 (off, on) |
| $DmaxG^S$ | Maximum GAP event duration | 3 S | 3–5s |
| $DmaxV^S$ | Maximum vascular event duration | 70 ms | |
| $DminG^S$ | Minimum GAP event duration | 2 ms | 2–5 ms |
| $DminV^S$ | Minimum vascular event duration | 20 ms | |
| $DT\_LN^S$ | Length of envelope data processing array | 1024 | A power of 2 |
| $DLY\_TH^S$ | Threshold of environmental sound delay | $ICDL\_L$ | max mic spcg/C air |
| $ENP\_PRE^S$ | The preset value of envelop threshold | 30 Mv | 25–100 Mv |
| $ENP\_SMT^S$ | Smooth envelope control | 0 | 0,1 (no, yes) |
| $FH^S$ | Low pass frequency | 1800 Hz | |
| $FL^S$ | High pass frequency | 70 Hz | |
| $FLTR\_B^S$ | Band pass filter control | 1 | 0,1 (no, yes) |
| $FmaxG^S$ | Maximum GAP event frequency | 1500 Hz | 800–1800 Hz |
| $FmaxV^S$ | Maximum vascular event frequency | 100 Hz | 30–120 Hz |
| $FminG^S$ | Minimum GAP event frequency | 20 Hz | 10–70 Hz |
| $FminV^S$ | Minimum vascular event frequency | 30 Hz | 5–30 Hz |
| $FO^S$ | Filter order | 3 | 1–50 |
| $FS^S$ | Sampling frequency | 4096 Hz | 2048 and up |
| $ICDL\_H^S$ | Upper limit of interchannel delay | 30 ms | function of C in abd. |
| $ICDL\_L^S$ | lower limit of interchannel delay | 0 ms | function of C in air |
| $K^S$ | Number of nearest neighbors | 4 or more | Number of subjects/3 |
| $OVLAP^S$ | Data overlap length | 14 | 5-$(DT\_LN^S/2)$ |
| $MU^S$ | Adaptation parameter | 5 | 0.01–10 |
| $N\_ENP^S$ | Number of envelope data points | $DT\_PTS$ | 1-$DT\_PTS$ |
| $N\_HST^S$ | Number of points of envelope histogram | 4094 | $2^{12}$ for 12-bit |
| $N\_SMTH^S$ | Number of points for data smoothing | 10 | 3–20 |
| $N\_STR^S$ | Number of structuring elements | 5 | 3–15 |
| $RL\_TH^S$ | Threshold on related events | 0.5 | 0.1–0.9 |
| $SPCG\_TH^S$ | Event spacing threshold for pasting | 30 ms | 5–30 ms |
| $SP\_TH^S$ | Threshold of the spectral deviation | 0.5 | 0.1–0.9 |
| $TYP^S$ | Type of structuring elements | 0 | 0,1 |

In addition, the sounds may be fed into the multichannel tape recorder in a step 206 which may then also feed the sounds to the analog amplifier filter 204. The amplifier filters and then feeds sounds to an analog to digital converter in the step 208 which converts the sounds to digitized sound signals for analysis by the computer in a step 210.

Figure 8:
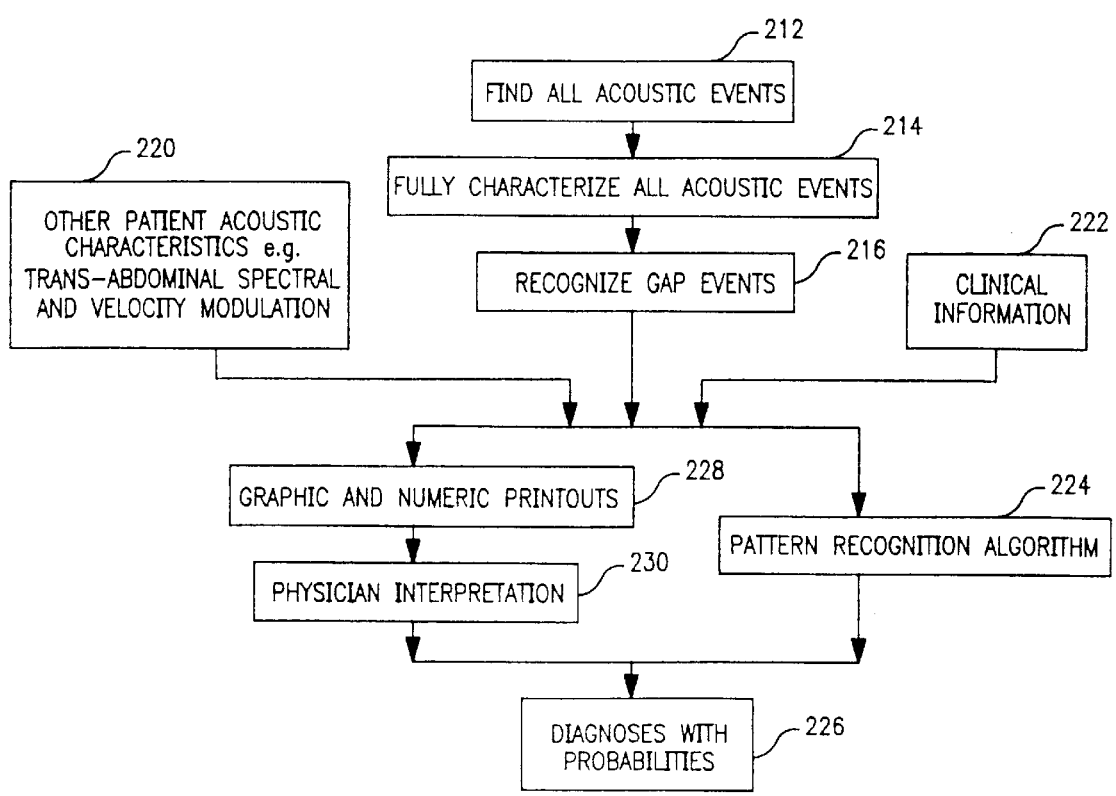
FIG. 8 is a flow diagram of a core process for processing gastrointestinal sounds.

As shown in FIG. 8, the computer is able to find acoustic events in a step 212 and to characterize the acoustic events in the step 214. It recognizes gastrointestinal acoustic phenomena (GAP) events in a step 216. In addition, from other portions of the routine other patient acoustic characteristics such as trans-abdominal spectra and velocity modulation are determined in a step 220. Clinical information may also be input through a keyboard or other appropriate means in a step 222, all of which are fed to a pattern recognition algorithm in a step 224 for providing diagnoses with probabilities in a step 226. In addition, the information received by the pattern recognition algorithm may be output in a step 228 and subject to physician interpretation in a step 230.

Figure 9:
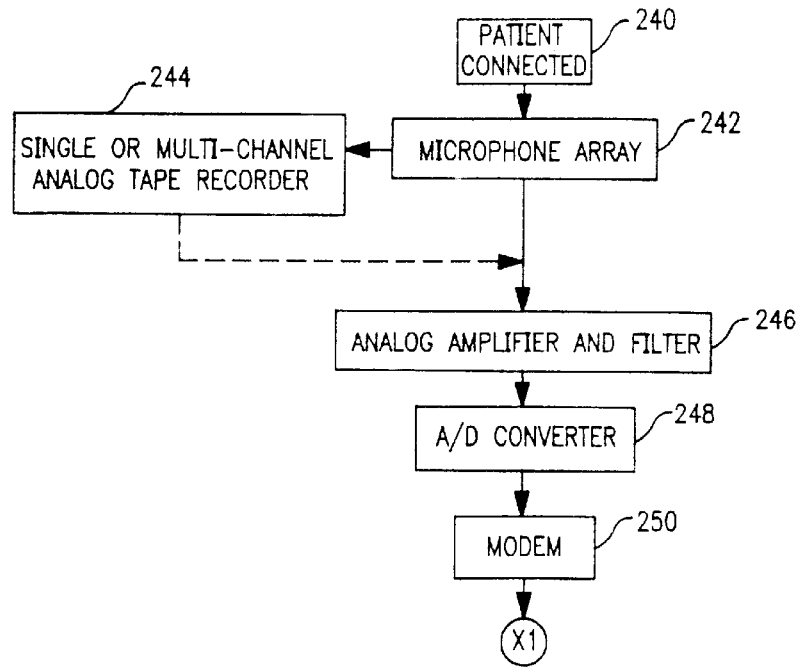
FIG. 9 is a flow diagram of a telemedicine version of the system.

In an alternative version as shown in FIG. 9, the patient may be attached to a microphone array in a step 240. The microphone array captures sounds in a step 242 and provides electrical signals to a single or multichannel analog tape recorder in a step 244 and also to an analog amplifier and filter in a step 246. The sounds are converted from analog form to digital form in a step 248 and the digitized sound signals may be provided to a modem in a step 250 for transmission to a centralized computer facility.

Figure 10:
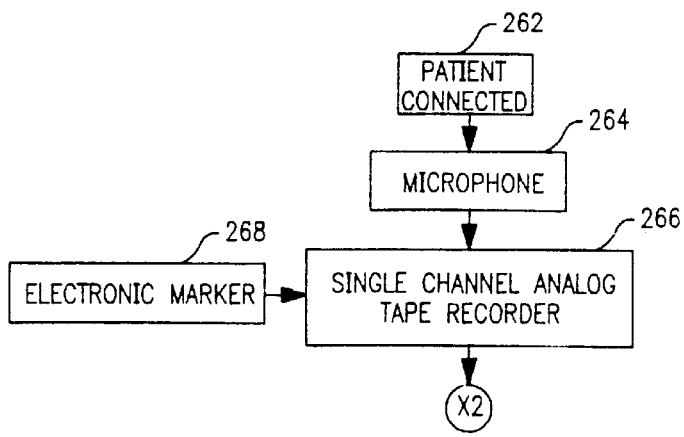
FIG. 10 is a flow diagram of a process for collecting ambulatory gastrointestinal sounds and storing them.

In an ambulatory monitoring system the patient may be connected to the microphone array in a step 262 as shown in FIG. 10. The microphone captures sounds in a step 264 and the sound signals are recorded by a single channel analog tape recorder in a step 266 for provision to other systems. The patient or the system may supply timing markers indicative of symptoms, events or time duration in a step 268. The same monitoring schema may also be used for long term monitoring over extended periods of time at low tape speed. In that case the electronic marker signal would comprise a timing signal impressed upon one of the channels. The timing signal would be used by digital processing to remove or reduce timing perturbations introduced by low speed flutter and wow in the tape recorder.

Figure 11:
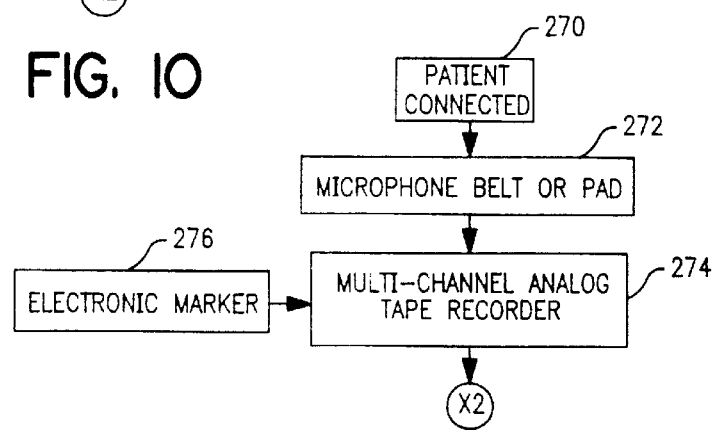
FIG. 11 is a flow diagram similar to FIG. 10 showing use of a multiple channel analog tape recorder in ambulatory settings.

In a still further alternative, as shown in FIG. 11, the patient may be connected to a microphone belt or pad in a step 270. The microphone belt or pad may convert the sound signals to analog signals in a step 272 and the analog sound signals are recorded in a step 274 for later provision to a computer. The patient or the system may supply timing markers indicative of symptoms, events or time duration in a step 276.

Figure 12:
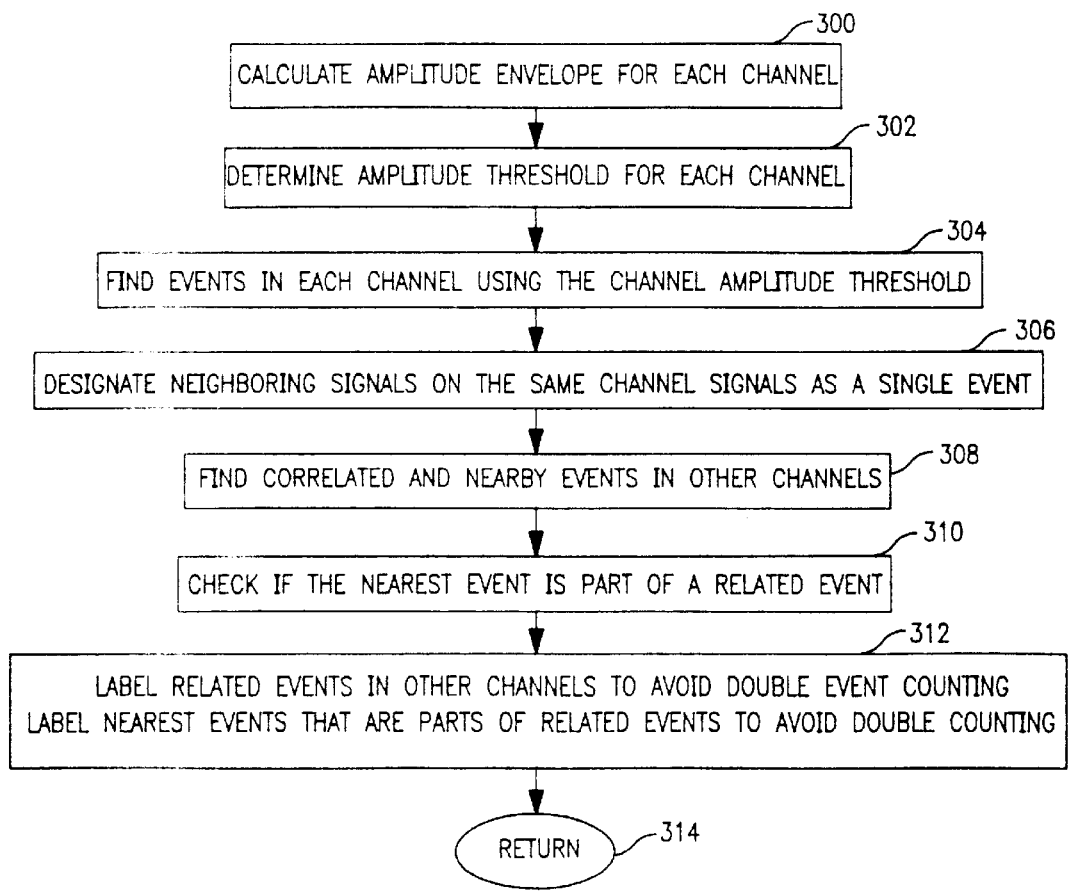
FIG. 12 is a flow diagram related to finding acoustic events and their features.

In general, as shown in FIG. 12, in order to find acoustic events and features in a step 300 the amplitude envelope is calculated for each of the sound channels. An amplitude threshold is then determined in a step 302 for each channel. In a step 304 the events in each channel are determined using the channel amplitude threshold by using the thresholding as a filtering or screening tool. In a step 306 neighboring signals are designated on the same channel signals as a single event. In a step 308 correlated and nearby events are determined in other channels. In a step 310 a determination is made whether the nearest event is part of an actually related event or is merely coincidental. In a step 312 related events are labeled in other channels to avoid double event counting and the nearest events that are part of related events are also labeled following which the return is exited in a step 314.

Figure 14A:
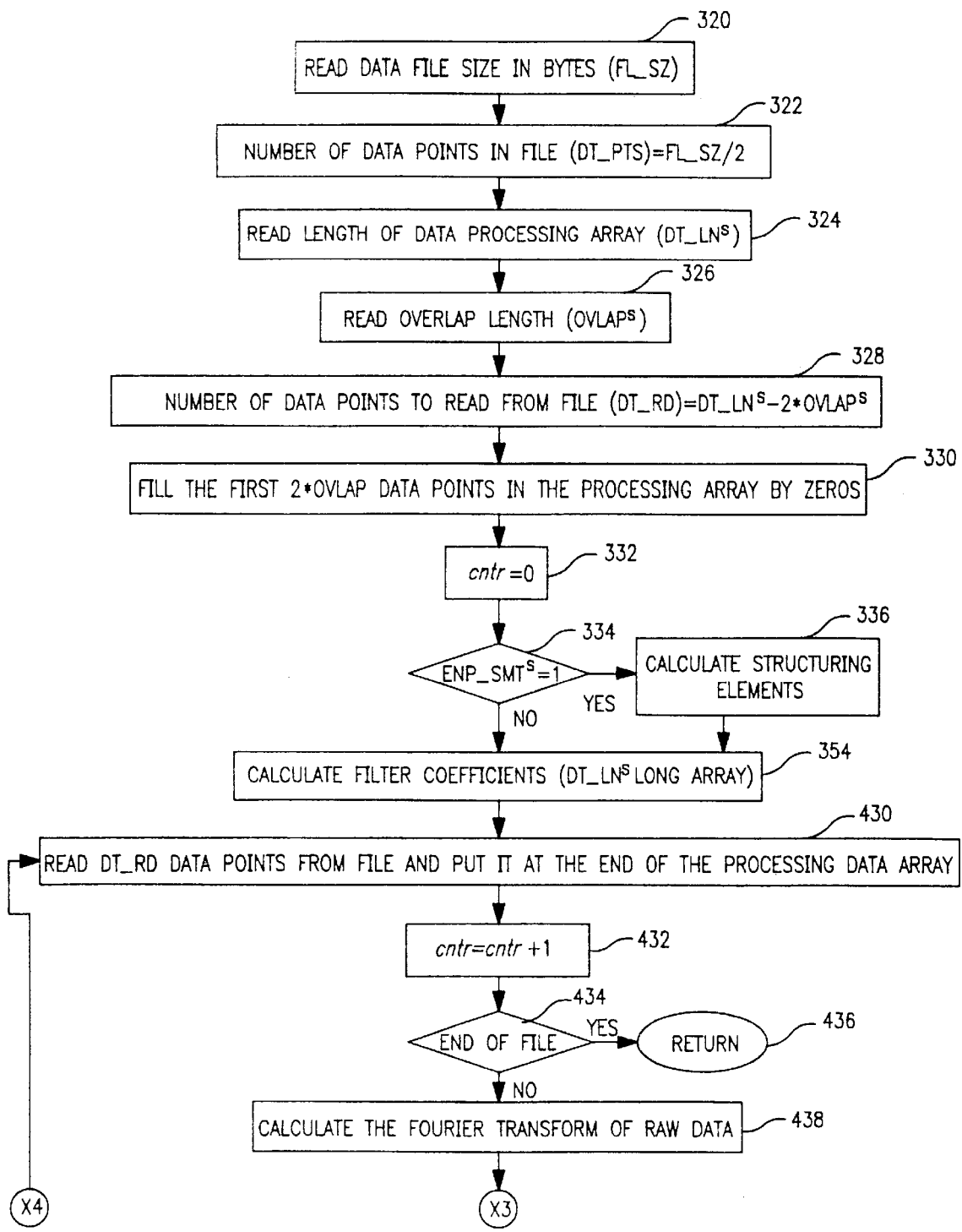
FIGS. 14a and 14b are flow diagrams for calculating a gastrointestinal sound envelope.
Figure 14B:
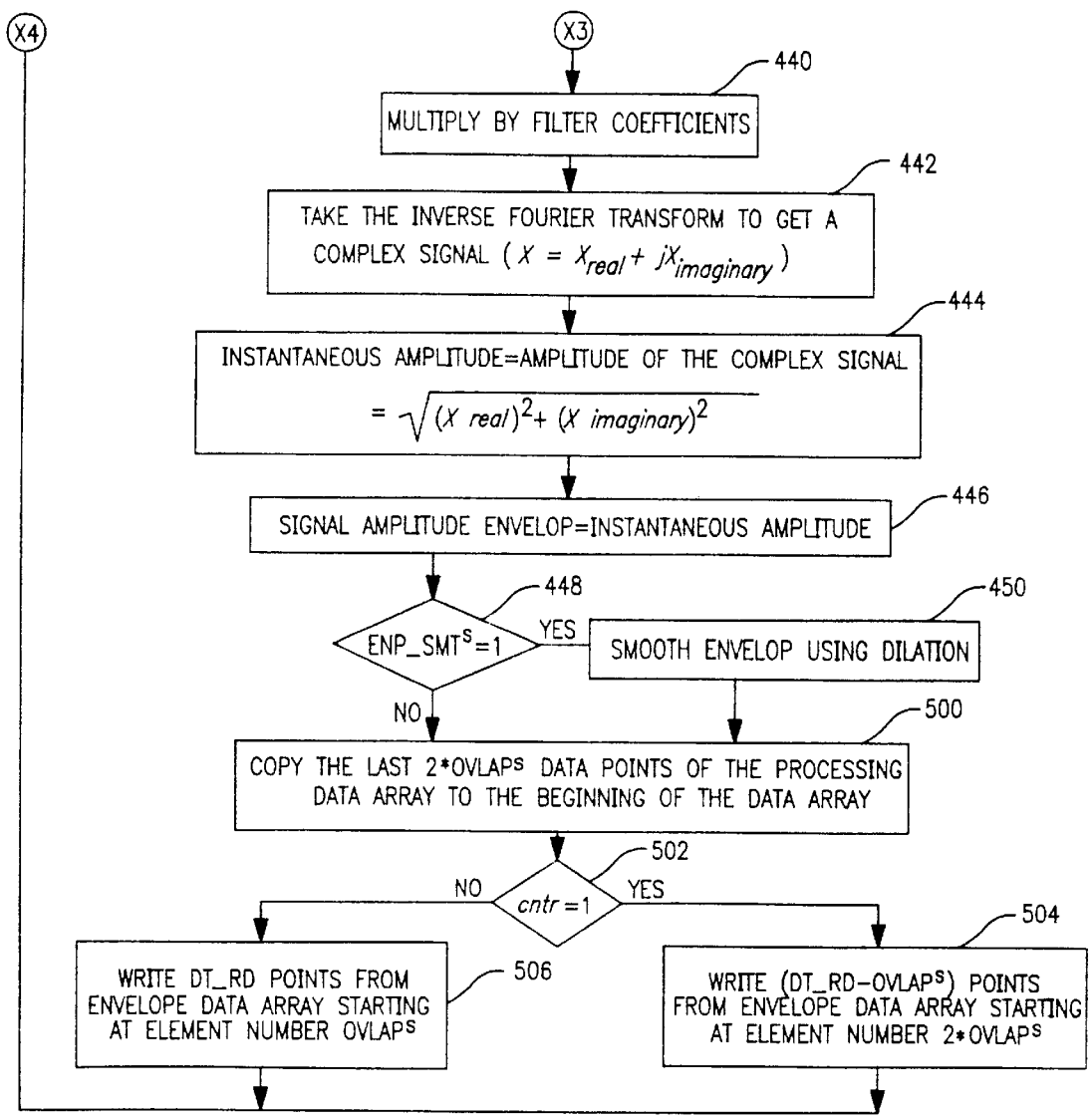

The step 300, involving the calculation of the amplitude envelope, is shown in further detail in FIGS. 14A through B. A data file stores the digitized sound signals and the file size is read in a step 320. The number of data points in the file is determined to be equal to the file size divided by 2 in a step 322. The length of the data processing array is then read from a variable indicator in a step 324 and an overlap length previously set is read in a step 326. The number of data points to be read from the file is calculated to be equal to the data processing array length minus two times the overlap length in a step 328. The first two times overlap length of data points in the processing array are packed with zeros in step 330 and the counter is set equal to zero in a step 332. A determination is made if the envelope smoothing flag is on in a step 334, and if it is, structuring elements are calculated in a step 336.

Figure 15:
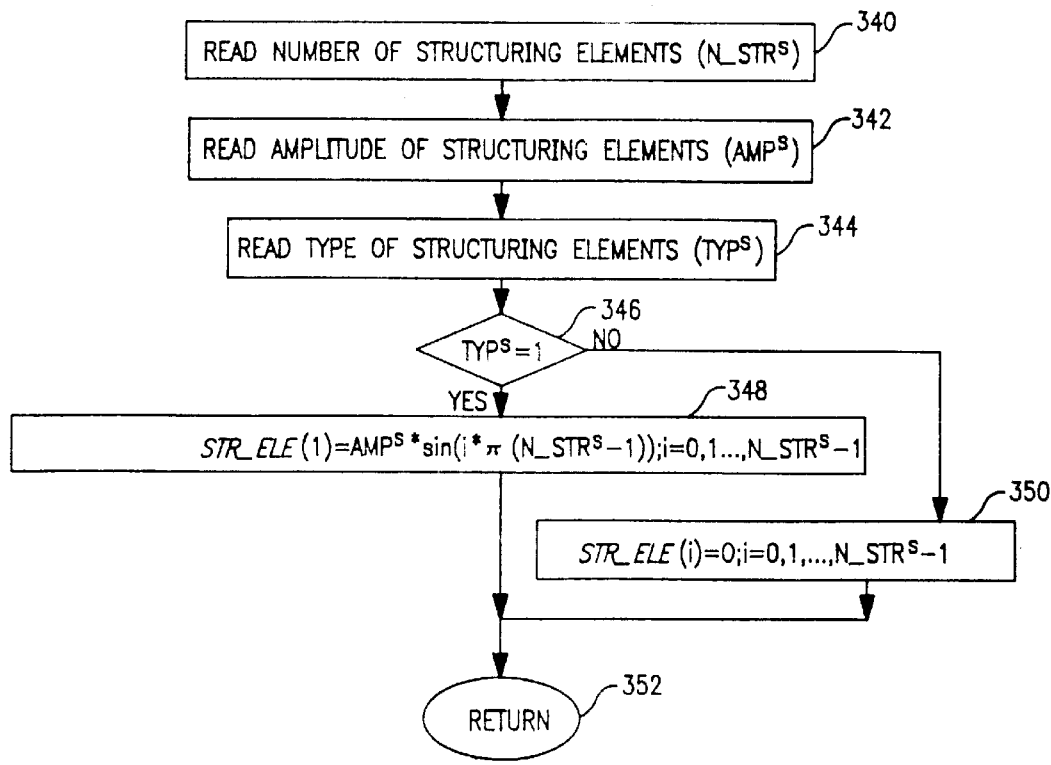
FIG. 15 is a flow diagram for calculating structuring elements.

Referring now to FIG. 15, the number of structuring elements is read in a step 340 and the amplitude of the structuring elements is read in a step 342. The type of the structuring elements previously determined is read in a step 344 and a type test is made in a step 346. If the structuring elements are of type 1 they are calculated according to structuring element equal to the amplitude times the size of the quantity i times π over number of structuring elements minus 1 taken from i=zero to the number of structuring elements in a step 348. If the type from 346 has been set equal to zero, the structuring element is packed with zeros in each of the elements of the array in a step 350 and the routine is exited in a step 352 to transfer control to a step 354 as shown in FIG. 14A to calculate the filter coefficients.

Figure 16:
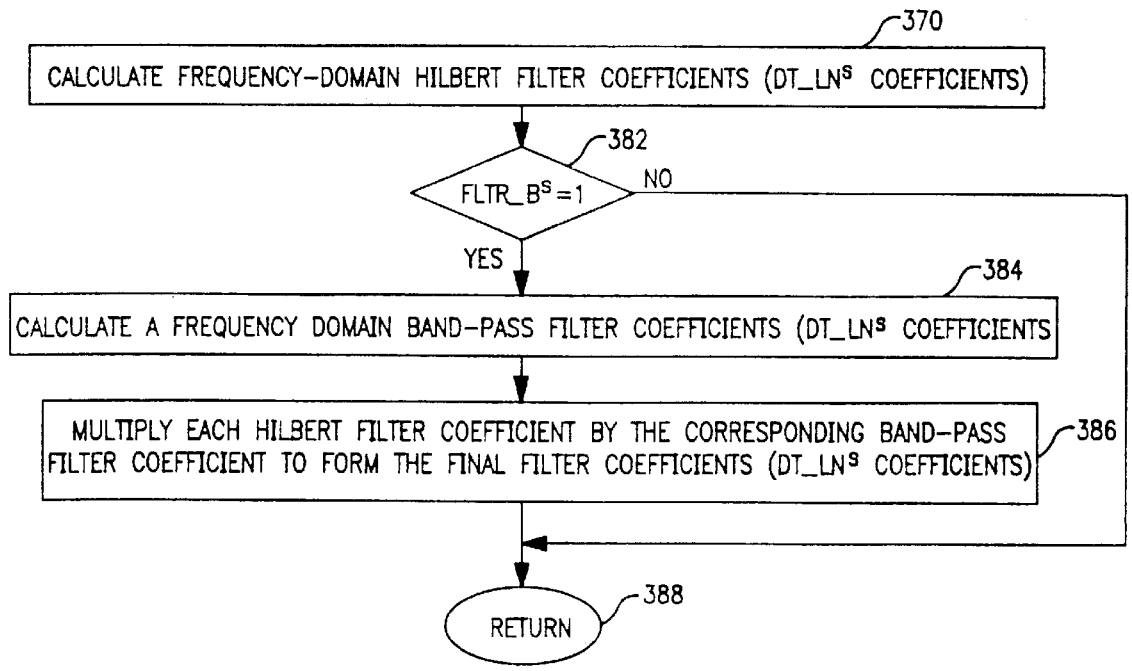
FIG. 16 is a flow diagram for calculating filter coefficients.

The filter coefficients are calculated in a routine as shown in FIG. 16 where the frequency domain filter coefficients are calculated in a step 370.

Figure 17:
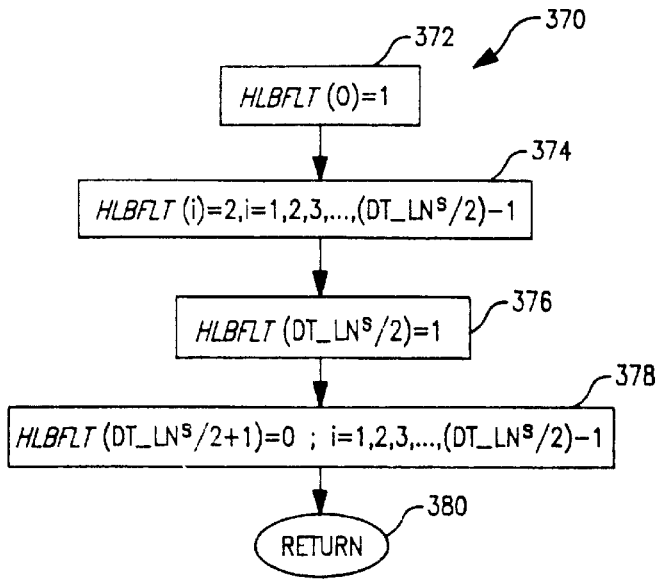
FIG. 17 is a flow diagram for calculating frequency domain Hilbert filter coefficients.

Step 370 is carried out as shown in FIG. 17 in a step 372 where the Hilbert filter coefficient zero is set equal to one and Hilbert filter coefficients one through half the data length minus 1 are set equal to two in a step 374. The next coefficient is set to one in a step 376. The last Hilbert filter coefficients are set equal to zero in a step 378 and return to step 380 to a step 382 shown in FIG. 16, The request of band pass filtering is tested in 382 and if found to be true, the frequency domain band pass filter coefficients are calculated in a step 384. In a step 386 each of the Hilbert filter coefficients is multiplied by a corresponding band pass filter coefficient to form a final filter coefficient following which the routine is exited in a step 388 to the prior routine.

Figure 18:
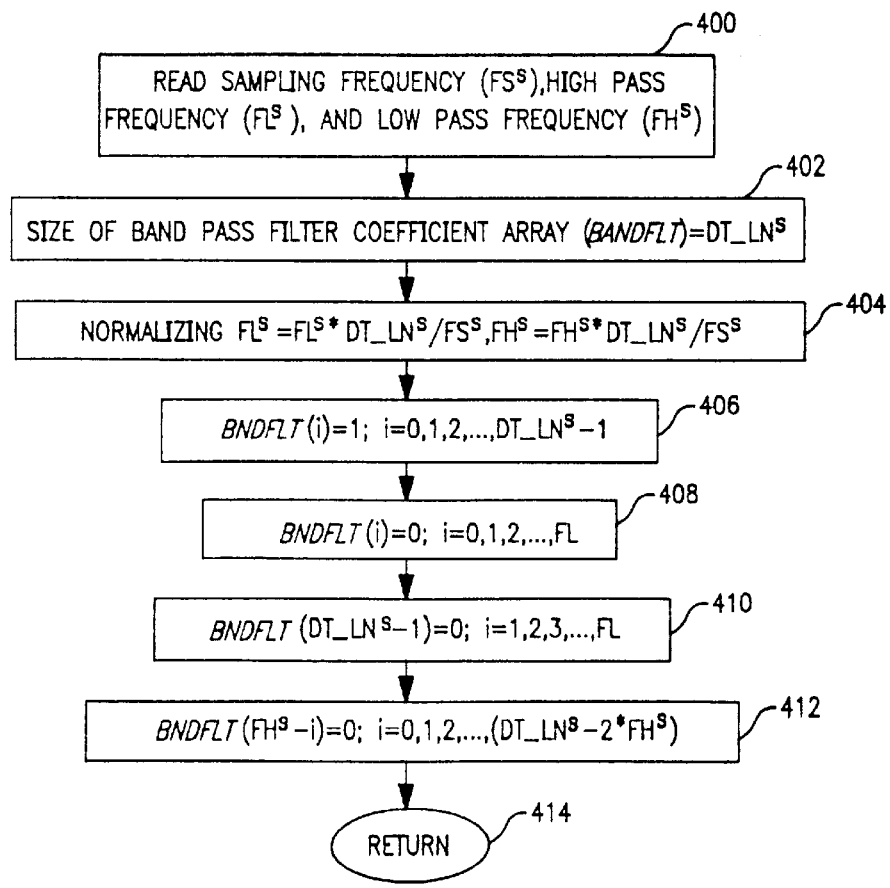
FIG. 18 is a flow diagram for calculating frequency domain band pass filter coefficients.

The step 384 is carried out in FIG. 18 wherein a step 400 the sampling frequency high pass frequency and low pass frequencies previously preset to 4096, 70 and 1800 Hz, respectively, are read. The size of the band pass filter coefficient is determined in a step 402 and normalizing occurs in a step 404. In steps 406 to 412 the band pass filter coefficients are computed and the routine is exited in a step 414 back to step 386 in the filter coefficient calculation routine shown in FIG. 16.

Referring now to FIG. 14A, the data points are read from the file and placed at the end of the processing array in a step 430. The counter is incremented in a step 432 and an end of file test is done in a step 434. If the file processing is ended, the routine is exited in a step 436. If not, a Fourier transform is calculated in a step 438 following which the transformed frequency domain function is multiplied by filter coefficients in a step 440, as shown in FIG. 14B. The inverse Fourier transform is taken in a step 442 to convert back to the time domain and the instantaneous amplitude of the complex signal is taken by taking the square root of the sum of the squares of the real and imaginary portions of the signal in a step 444. The signal envelope is set equal to the instantaneous amplitude in step 446 and a test is made in a step 448.

Figure 19:
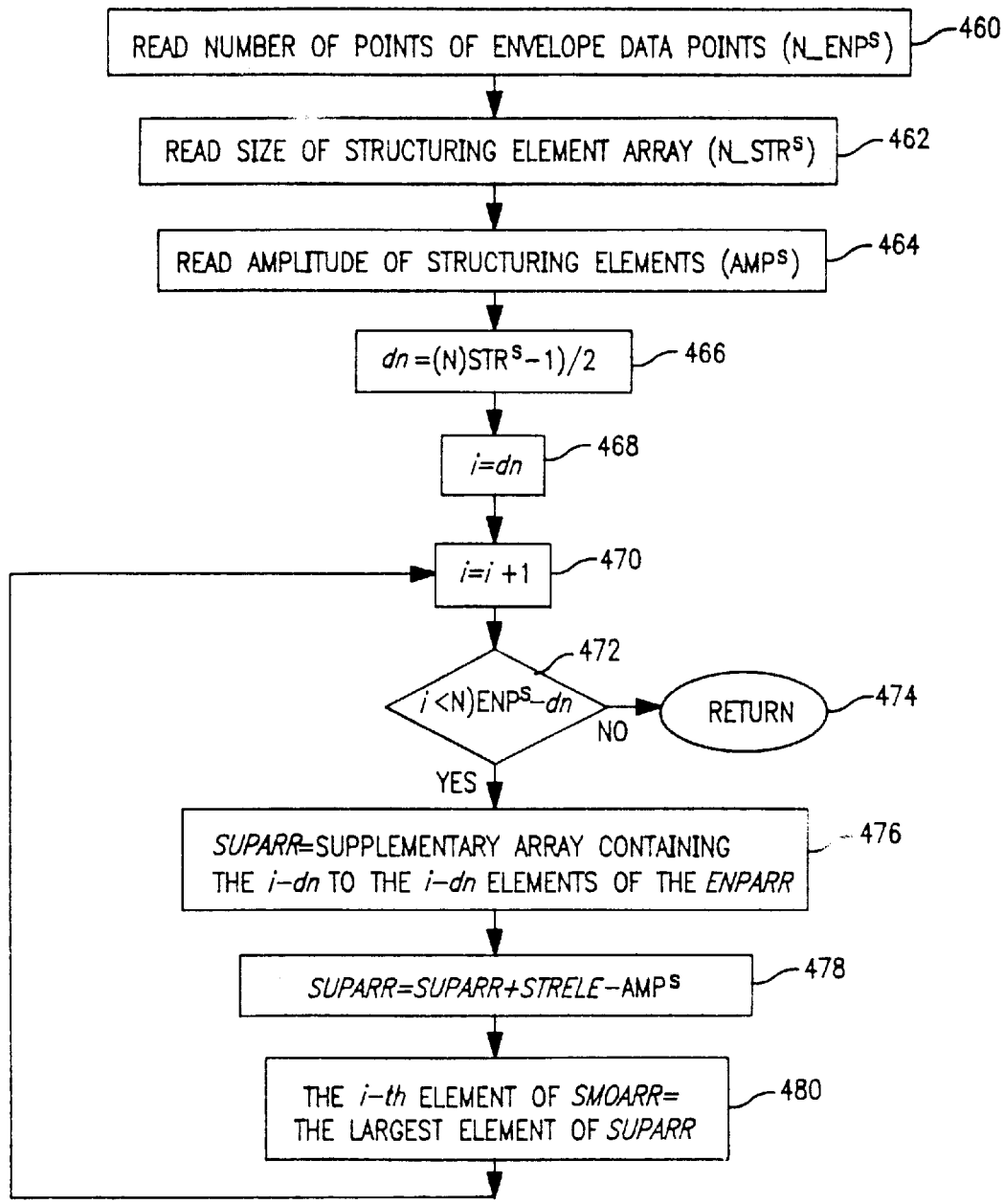
FIG. 19 is a flow diagram for an envelope smoothing process using dilation.

If the test is positive the envelope is smoothed using dilation in a step 450 as may be seen in further detail in FIG. 19 wherein the number of data points of the envelope is read in a step 460. The size of the structuring element is read in step 462. The amplitude of the structuring element is read in step 464 and a variable dn is set equal to the structuring element length less one, the whole quantity divided by two in a step 466 That quantity is assigned to a counter in a step 468 and the counter is incremented in a step 470. A test is then made to determine whether the number of points is between the original dn number from step 464 or the current counter number in a step 472. If it is not, the step is returned from in a step 474. If it is, a supplementary array is loaded in a step 476. The supplementary array is updated in a step 478 and the $i_{th}$ element of the array is determined in a step 480 following which the routine loops back to the counter in step 470.

In the event that the envelope is not to be smoothed or the step 450 is completed as shown in FIG. 14B, the last two times the overlap length of data points of processing data array is copied into the beginning of the array in a step 500. A test is made to determine whether the counter is equal to one in a step 502. If it is, a number of the data envelope points, equal to the read data points minus the overlap length, starting at two times the overlap length is written to an output file in a step 501. In the event that the counter is not equal to one the points are written to the output file from the envelope data array starting at envelope element overlap in a step 506, following which the control is transferred back to step 430.

Figure 20:
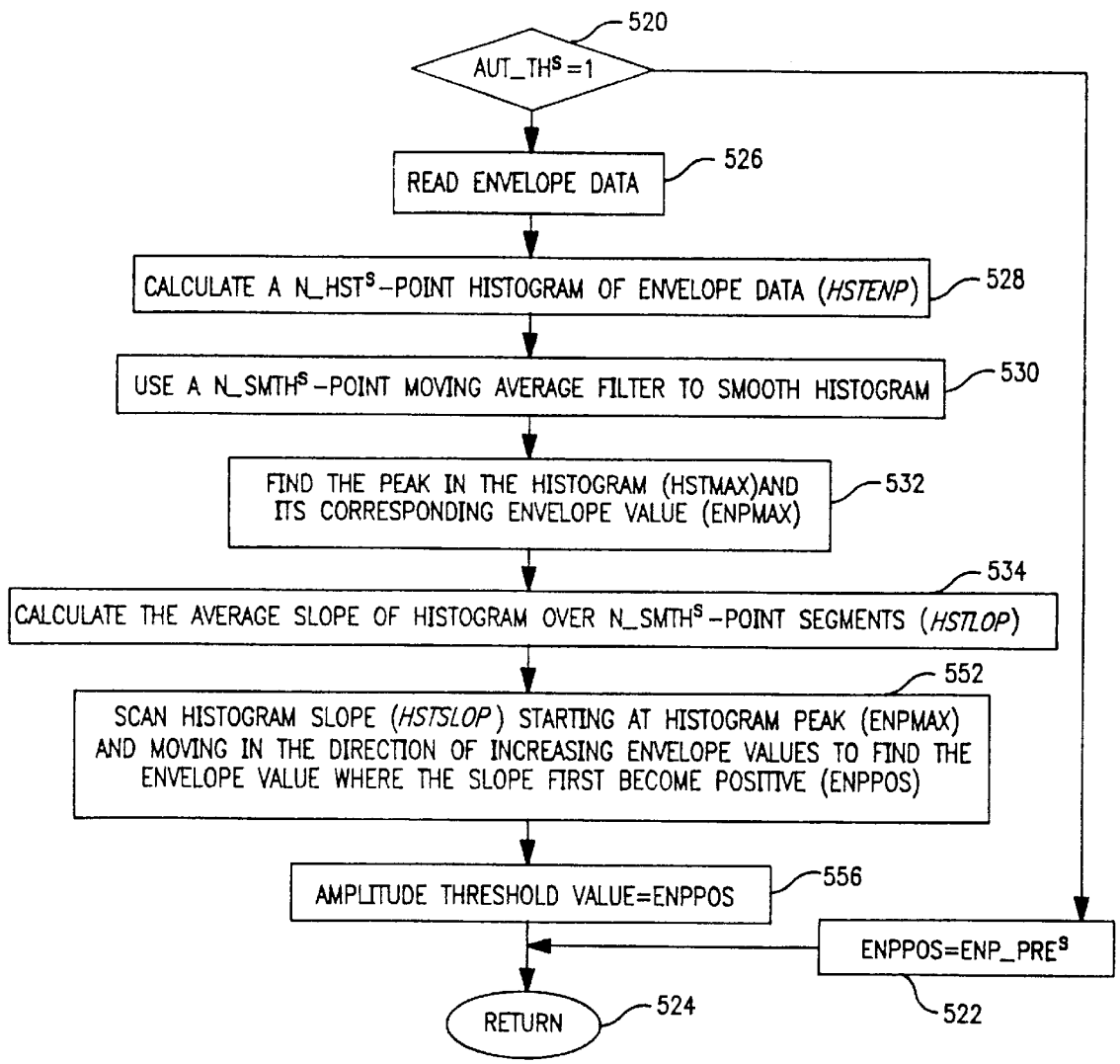
FIG. 20 is a flow diagram for determining the amplitude threshold.

In order to perform the amplitude threshold determining step for each channel, step 302 shown in FIG. 12, an amplitude threshold routine is provided as set forth in FIG. 20. In a step 520 a test is made to determine whether the amplitude threshold has previously been set. If it has, the end position is set equal to the preset in a step 522, following which the routine is exited in a step 524. If it has not, the envelope data is read in a step 526 and a histogram of the envelope data is constructed in a step 528, as shown in greater detail in FIG. 21. A smoothing moving average filter is applied to the histogram data in the step 530 and the peak on histogram and corresponding envelope value are determined in the step 532. The average slope of the histogram over data segments of preselected length is determined in a step 534 which is shown in greater detail in FIG. 22, wherein in a step 540 the first envelope value is determined. In a step 542 the slope is set equal to the current envelope value minus the next envelope value. An end of data test is made in a step 544. If the end of data has not been reached, the next envelope value is considered in a step 546 following which control is returned to step 542. If it has not, a moving average filter is applied in a step 548 to smooth the slope, following which the routine is exited in a step 550, returning control to a step 552 shown in FIG. 20. When the histogram slope values are scanned starting at the histogram peak and moving in the direction of increasing envelope values to find an envelope value where the slope first becomes positive Upon finding the value when the slope first becomes positive, the amplitude threshold value is set equal to that value in a step 556 and the routine is exited in step 524.

Figure 21:
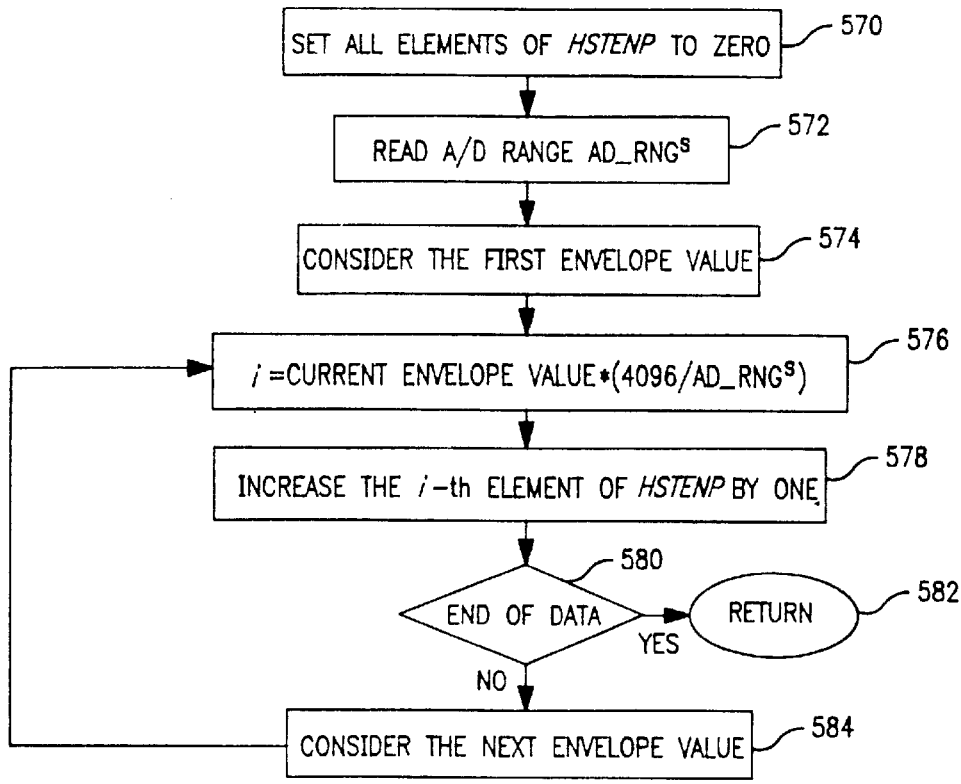
FIG. 21 is a flow diagram for producing a histogram of the envelope.
Figure 22:
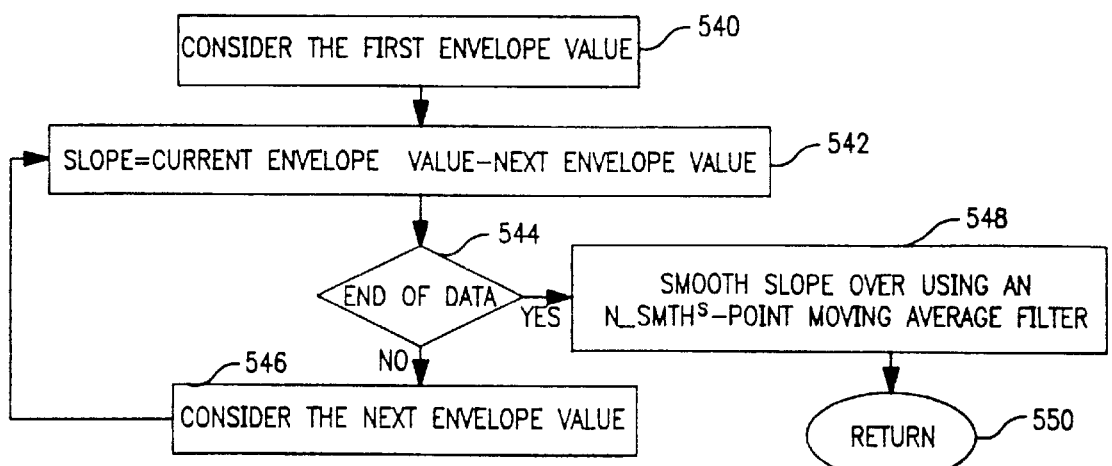
FIG. 22 is a flow diagram for calculating a smoothed average slope of the histogram.
Figure 23:
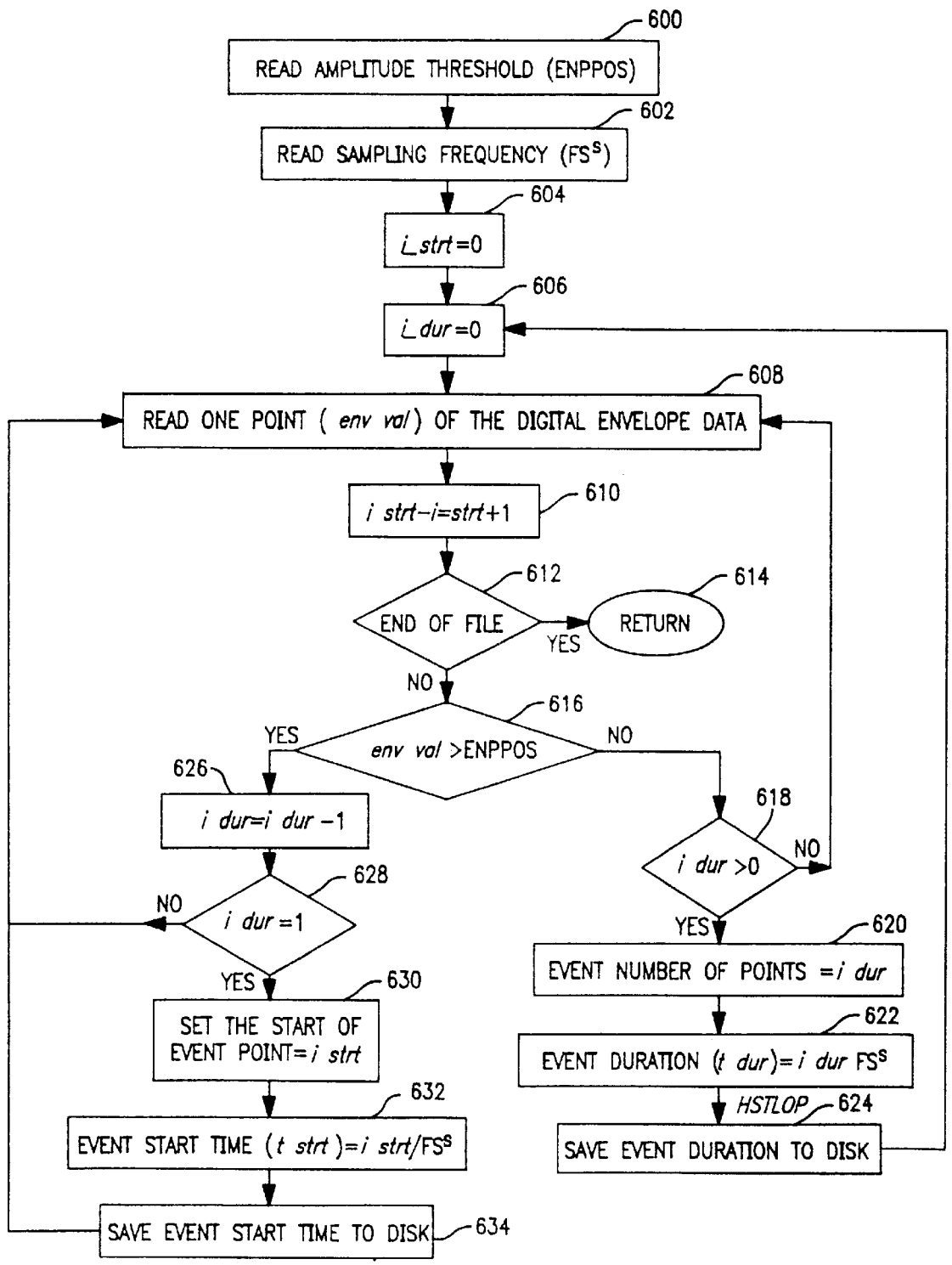
FIG. 23 is a flow diagram for finding gastrointestinal sound events in each channel.

In order to calculate the histogram of the step 528, as shown in FIG. 21, all elements of the histogram array are set equal to zero in a step 570. The ADD range previously set is read in a step 572 and the first envelope value is considered in step 574. Variable i is set equal to the current envelope value times the quantity 4,096 divided by the analog to digital converter range in a step 576 and in a step 578 the $i_{th}$ element of the histogram vector is increased by one step to the next point. An end of data test is made in a step 580. If the end of data has been reached the routine is exited in return step 582. If not, control is transferred to a step 584 causing the next envelope value to be considered and then transferring control back to step 576.

After the amplitude threshold for each channel has been found in step 302, events in each channel must be located using the channel amplitude threshold in the step 304. This is carried out in the routine shown in FIG. 23 wherein in a step 600 the amplitude threshold value previously calculated is read as is a preset sampling frequency. The variable i__strt is set equal to zero in step 604; and the variable i__dur is set equal to zero in step 606. First point of the digital envelope data is read in a step 608 and the i__strt value is incremented in a step 610 following which an end of file determination is made in a step 612. If the end of file has been reached control is transferred to a step 614. If it has not, the envelope value is tested for whether it is greater than the amplitude threshold; in other words, is there a real reading or a noise reading in a step 616. If it is not, control is transferred to a test to determine whether i__dur is greater than zero in a step 618. If i__dur is not greater than zero, control is transferred back to step 608, causing the next data point to be read. If i__dur is greater than zero, the event number of points is set equal to i__dur in the step 620. The event duration is set equal to the event number of points divided by the sampling frequency in the step 622 and the event duration is saved to disk in a step 624 following which step 606 is executed.

If the event value is greater than the great amplitude threshold, control is transferred from step 616 to a step 626 causing the duration variable to be incremented. A test is made to determine whether the duration value variable is equal to one in a step 628. If it is not, control is transferred back to step 608. If it is, the starting point of the event is set equal to i__start in a step 630. The event start time is set equal to i__start divided by the sampling frequency in a step 632. The event start time is then saved to disk in a step 634 following which the next point of the digital envelope data is read in a step 608.

Figure 24:
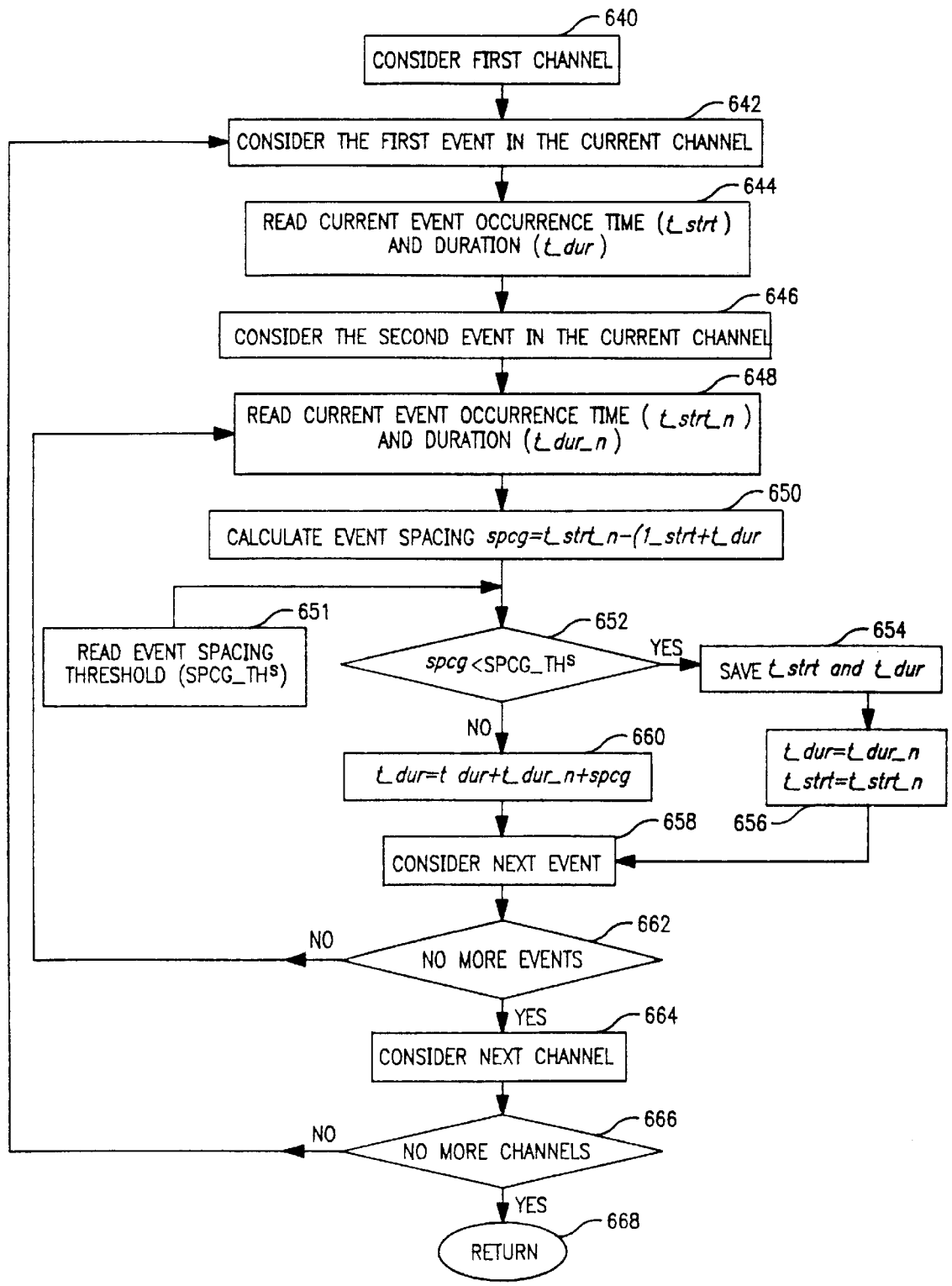
FIG. 24 is a flow diagram for pasting neighboring signals on the same channel into a single event.

In order to perform Step 306 where neighboring signals, which are neighboring in time are designated on the same channel signals as belonging to a single gastrointestinal acoustic phenomenon or event, as is shown in FIG. 24 the signals from the first channel are accessed in a step 640. The first event, which has been previously identified, is accessed in a step 642 The current event occurrence time and duration previously determined are accessed in a step 644 and the second event in the channel is accessed in a step 646. The current event occurrence time and durations for the second event are accessed in a step 648 and the event spacing spcg is calculated in a step 650. In a step 652 if the calculated event spacing is less than a threshold event spacing, control is transferred to a step 654 and the event occurrence time and duration are saved in a step 654 and the second event's occurrence time and duration are stored as the event occurrence and duration in a step 656 following which in a step 658 the next event is considered. In the event that the spacing is less than the threshold, in a step 660 a new duration is calculated as the sum of the spacing the second event duration and the original duration, and the next event is then considered in a step 658. Following step 658 a test is made to determine whether any more events are present. If they are not, in step 662 control is transferred to a step 664, causing the next channel to be analyzed as set forth in the previous steps. A test is then made in a step 666 to determine whether any additional channels need to be analyzed. If there are no more channels to be analyzed, the routine is exited in a step 668. If there are more channels to be analyzed, control is transferred back to step 642.

Figure 25:
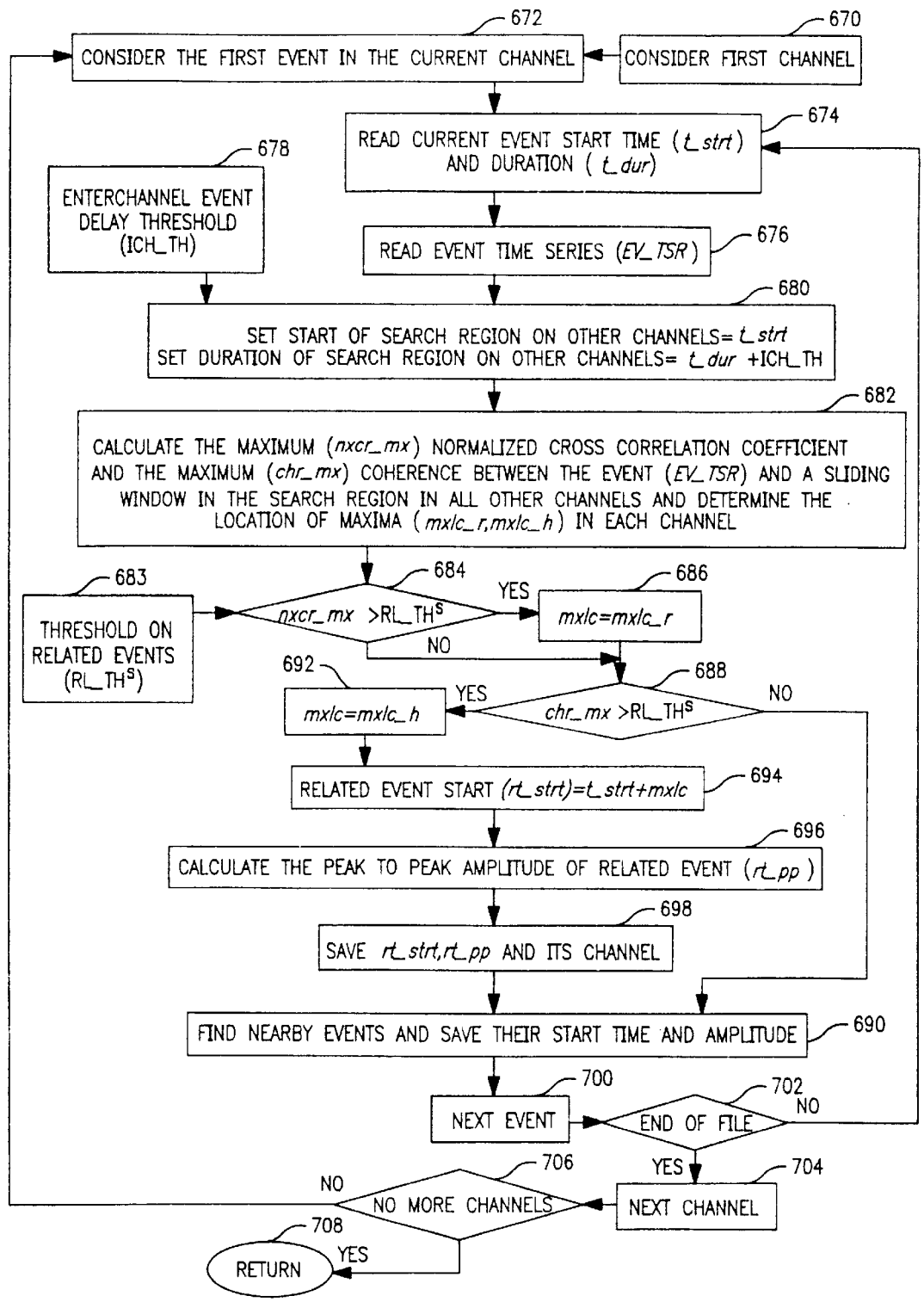
FIG. 25 is a flow diagram for finding related events in other channels.

In order to find correlated in nearby gastro-acoustical phenomenon or events in other channels as set forth in step 308 shown in FIG. 12, the steps shown in FIG. 25 are performed.

Figure 26:
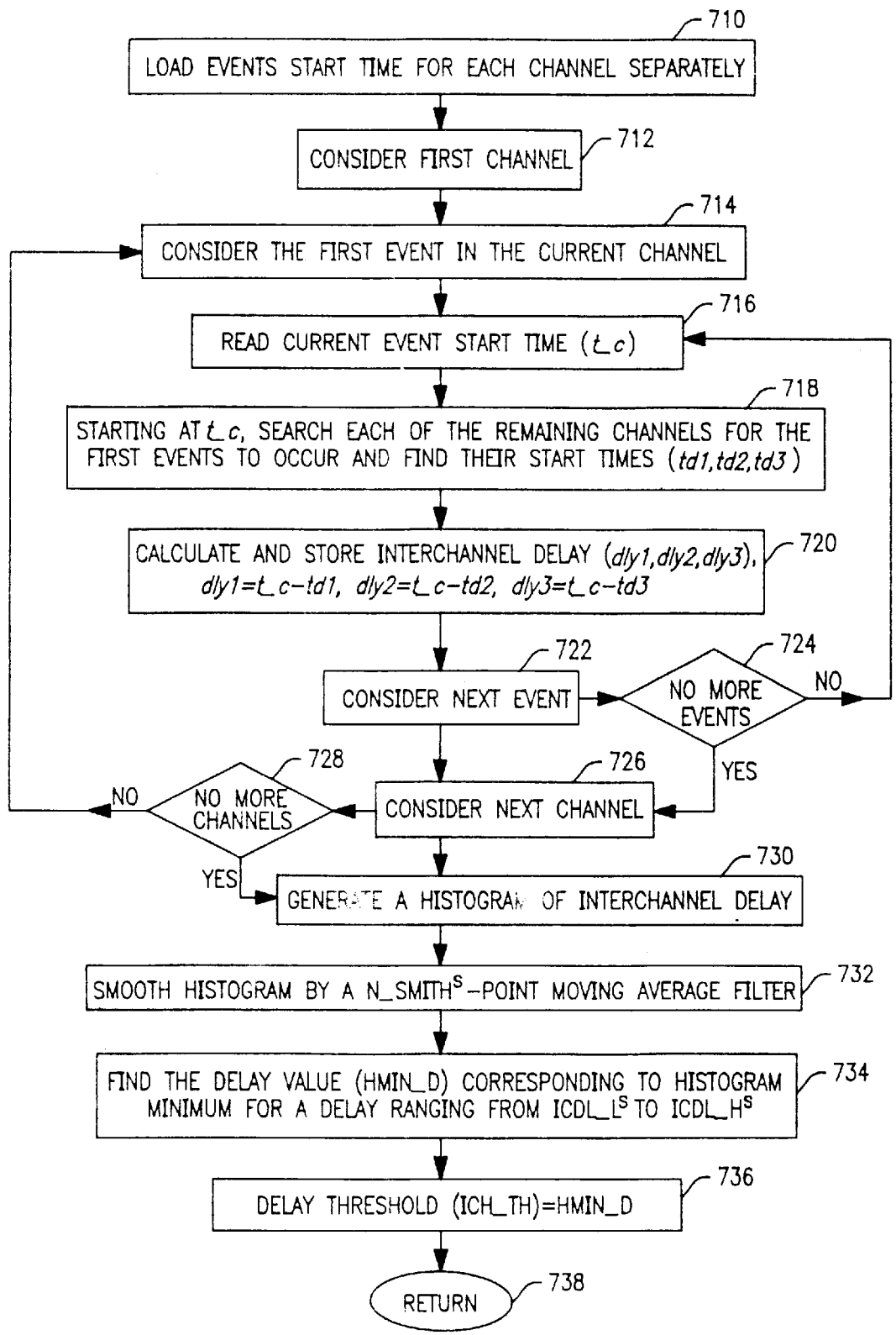
FIG. 26 is a flow diagram for determining an interchannel event delay threshold.

The first channel is taken under consideration in the step 670 and in a step 672, the first event is to be examined. In a step 674 the current event start time and its duration are read and in a step 676 the event time series is read. In addition, in a step 678 the interchannel event delay threshold, which is determined as set forth in FIG. 26, is read. In a step 680 the search region on other channels is set as well as the search duration which is dependent upon the interchannel event delay threshold. In a step 682 the maximum normalized cross-correlation coefficient and maximum coherence between the events and the sliding window in the search region and in other channels for use in determining the location of Maximum on each channel is calculated. In the event that the maximum normalized cross correlation coefficient exceeds a threshold on related events previously set in a step 683, control is transferred in a step 684 to a step 686, causing a holding variable to be located with the location of the maximum. In the event the test in the step 684 is negative, control is transferred directly to a step 688, causing a test to be made to determine whether the maximum coherence between the event and the sliding window in the search region is greater than a threshold on related events. If it is, the second local maximum location is loaded in step 692. If it is not, control is transferred to a step 690, causing nearby events to be found and their start times to be saved, as set forth in FIG. 27 and described hereinafter. Control is then transferred to a step 700 where the next event is accessed and processed. A test is made in a step 702 for end of file. If end of file has not been reached, control is transferred back to step 674. If the end of file for that channel has been reached, control is transferred to a step 704, causing the next channel to be incremented to and a test is made in a step 706 to determine whether any more channel information is available. If it is, control is transferred back to step 672 for further processing. If it is not, control is transferred to a step 708, following which the routine is exited and control is transferred back to step 310 to determine whether the nearest event is part of a related event.

Referring now to FIG. 26, the steps for determining the interchannel event delay threshold, which has been previously applied or set forth therein, in a step 710 the event start time for each of the channels is loaded separately and then consideration is shifted to the first channel in a step 712. The first event is accessed in a step 714 and current event start time is read in a step 716. Starting at the current event start time a search is made along each of the other channels for the first event to occur and their individual start times are determined. Interchannel delays are calculated as being the difference between each of the other channel start times and the current event start time in a step 720. In a step 722 indexing is done to the next event and a test is made in a step 724 to determine whether any more events are present on that channel. If they are not, control is transferred to a step 726 where indexing is done to the next channel, and a test is made in a step 728 to determine whether any more channels of data are available. If there are more channels of the data, control is transferred back to step 714. If there are no more channels of data to be processed, a histogram of the interchannel delay is generated in a step 730. The histogram is smoothed, with a smoothing average filter in a step 732 and a delay value corresponding to the histogram minimum for delay ranging between preset high and low values is determined in a step 734. The delayed threshold is then set equal to the delay value in a step 736 and routine is exited in a step 738.

Figure 27:
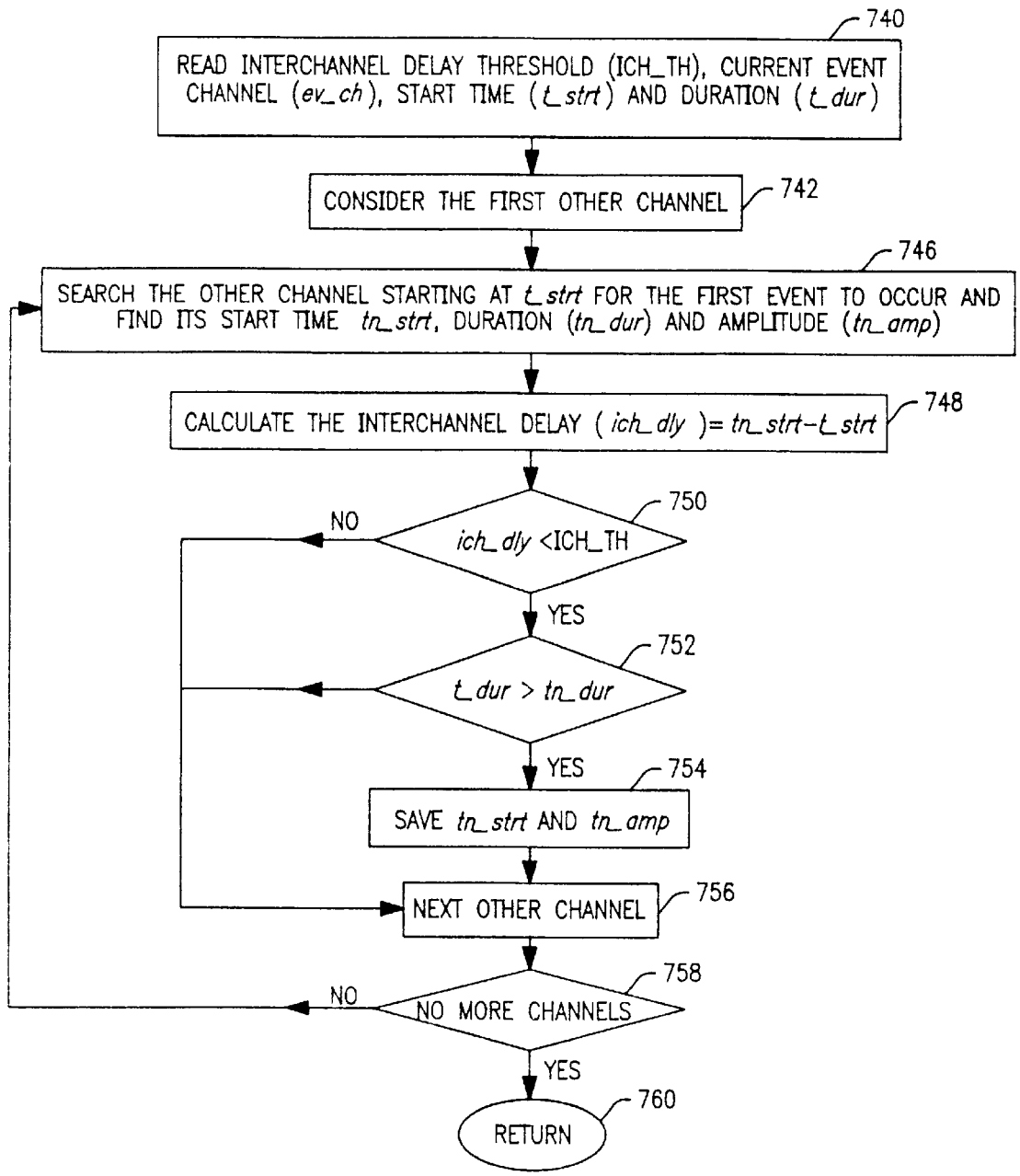
FIG. 27 is a flow diagram for finding nearby events and saving their time and amplitude.

In order to find nearby events and save their start times and their amplitudes as required in step 690 appearing on FIG. 25, the process set forth in FIG. 27 is employed. In a step 740 the interchannel delay threshold previously determined, the current event channel, the start time and the duration are all read. The first channel is considered in the step 742 and in a step 746 other channels starting at the starting time for the first event are searched and the events' start time, duration and amplitude are found. The interchannel delay is then calculated in a step 748 as being the difference between the initial start time and the first event start time. A test is made in a step 750 to determine whether the interchannel delay is less than the interchannel delay threshold. If it is, control is transferred to a step 752 in which a test is made to determine whether the current event duration is greater than the first event duration on the other channel. If the current event duration is greater than the first event duration on the other channel, control is transferred to a step 754, causing the start time of the first event on the other channel and its amplitude to be saved. If the responses to step 750 and 752 are either in the negative, control is transferred to a step 756 causing the next channel to be accessed and processed. Control is then transferred to a step 758, checking for additional channels to be processed. If there are no more channels the routine is exited in a step 760. If there are more channels to be processed, control is transferred back to the step 746.

Figure 28:
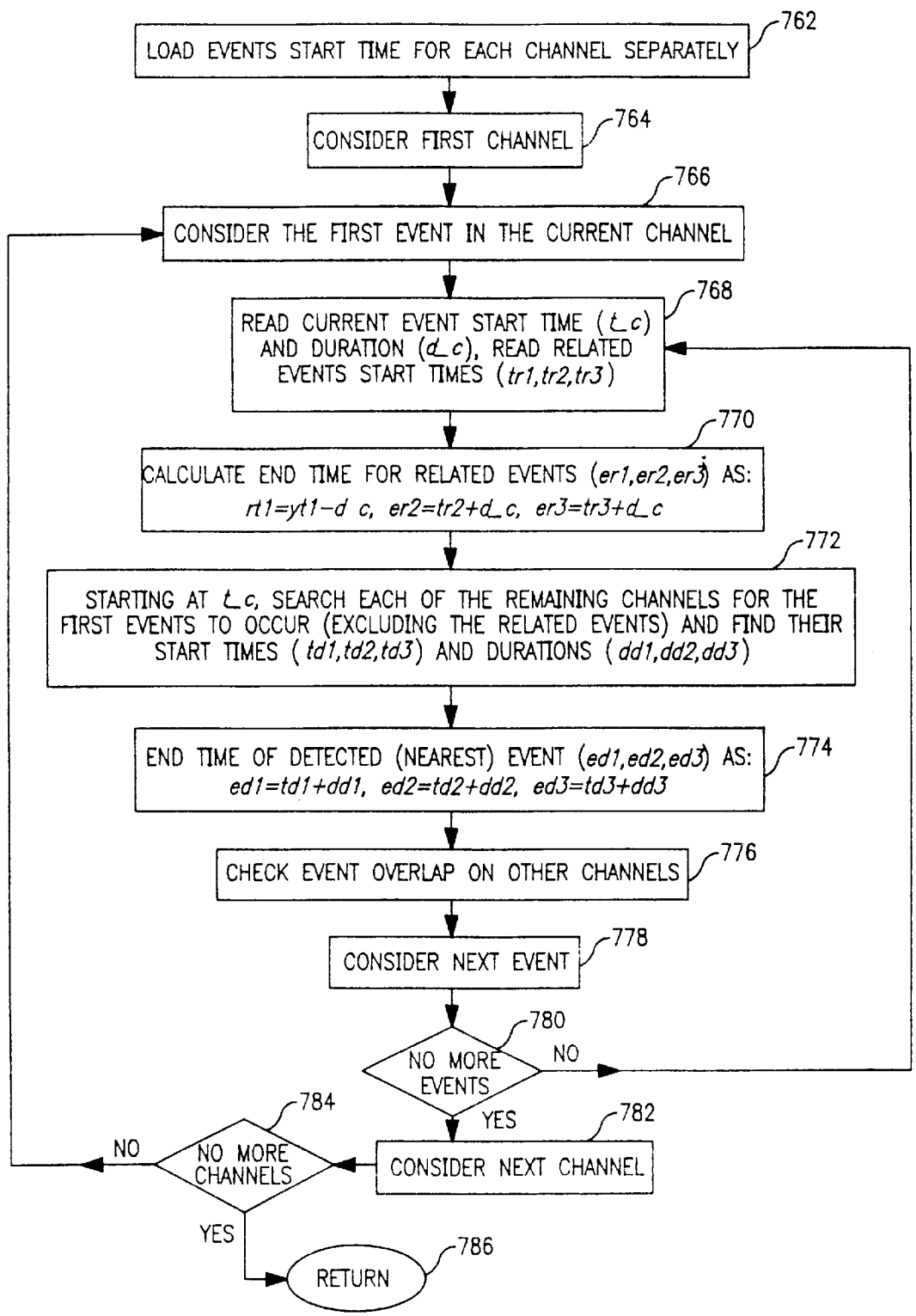
FIG. 28 is a flow diagram of a checking process for determining whether a nearest event is part of a related gastrointestinal event.

In order to perform the step 310 in which a check is made to determine if the nearest event is part of a related event, the routine set forth in FIG. 28 is carried out. In a step 762 the event start time for each channel is loaded and the first channel is considered in a step 764. The first event in the current channel is accessed in a step 766 and the current event start time and its duration are read. Related event start times are also read, all in a step 768. The end time for the related events is calculated as a different between the related event start times and the current event start time. Beginning at the current event start time, each of the remaining channels is searched for the first events to occur other than related events and their start times and durations are determined. The end time of the nearest detected event is determined in a step 774 and the event overlap on channels is checked in a step 776 as set forth in further detail in FIG. 29. The next event is considered in a step 778 and a test is made in a step 780 to determine whether there are more events. If there are more events, control is transferred back to step 768. If there are not, the next channel is accessed in step 782. An end of channel test is made in a step 784. If the end of channel's test indicates further channels are to be processed, control is transferred to a step 766. If not, the routine is exited in a step 786.

Figure 29:
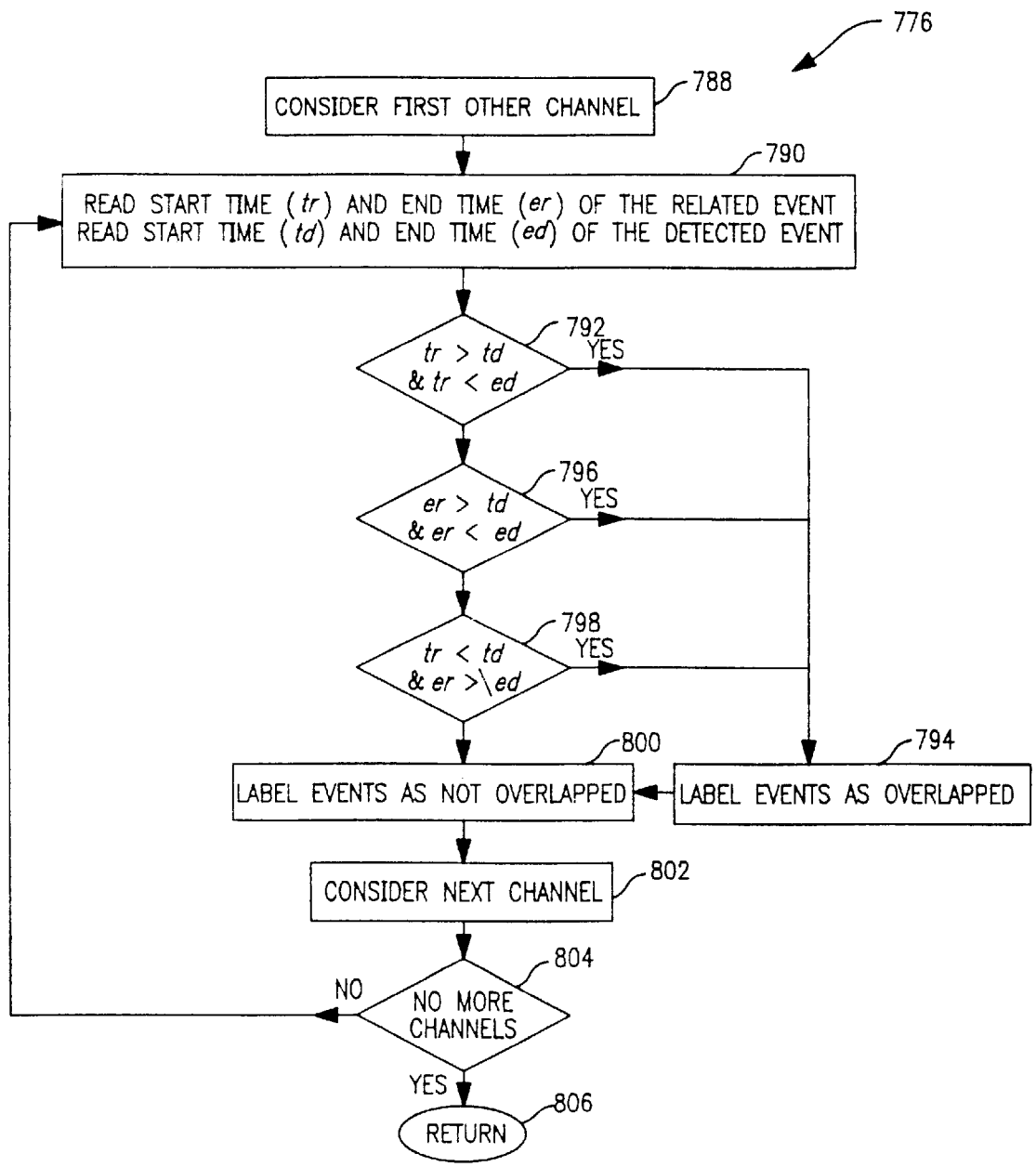
FIG. 29 is a flow diagram for checking gastrointestinal event overlap on other channels.

The step 776 is performed as set forth in FIG. 29. The first channel is considered in a step 788 and the start time and end time of the related events as well as the start time and end time of the detected event are obtained in step 790 from storage. A test is made in a step 792 to determine whether the start time of the related event is greater than the start time of the detected event and whether the start time of the related event is less than the end time of the detected event. If it is, control is transferred to a step 794, causing the events to be labeled as overlapped. If it is not, control is transferred to a step 796 wherein the end time of the related event is tested to determine whether it is greater than the start time of the detected event together with the end time of the related event being tested to determine whether it is less than the end time of the detected event. If both of those equalities are true, control is transferred to step 794 and the events are labeled as overlapped. If not, control is transferred to step 798 wherein a test is made to determine whether the start time of the related event is less than the start time of the detected event and the end time of the related event is greater than the end time of the detected event. If true, the events are labeled as overlap in step 794. If not, control is transferred to step 800 and the events are labeled as not overlapped, following which in a step 802, the next channel is considered. A test is made in a step 804 to determine whether any more channels are to be examined. If they are to be examined, control is transferred back to step 790. If they are not, the routine is exited in a step 806.

Figure 13:
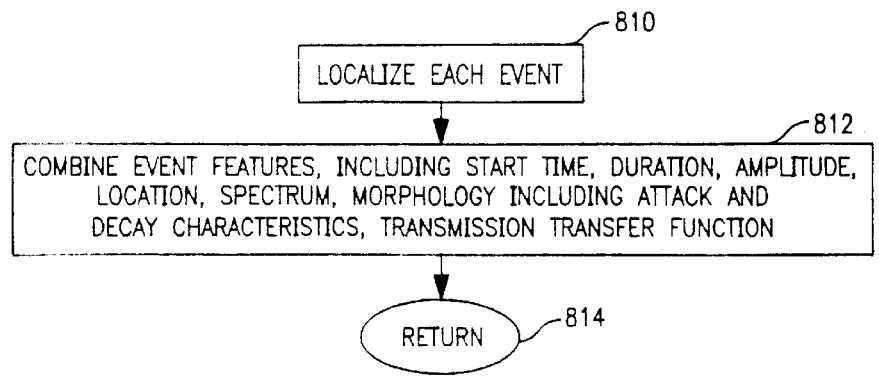
FIG. 13 is a flow diagram related to localization and characterization of gastrointestinal acoustic events.

In addition, it is important to characterize the events once they have been identified as set forth in FIG. 13, in a step 810 a test is made to localize each event followed by which in a step 812 event features are combined, including a start time, duration, amplitude, location, spectrum, morphological characteristics, including attack and delay characteristic, and a transmission transfer function followed by exiting the routine in a step 814.

Figure 30:
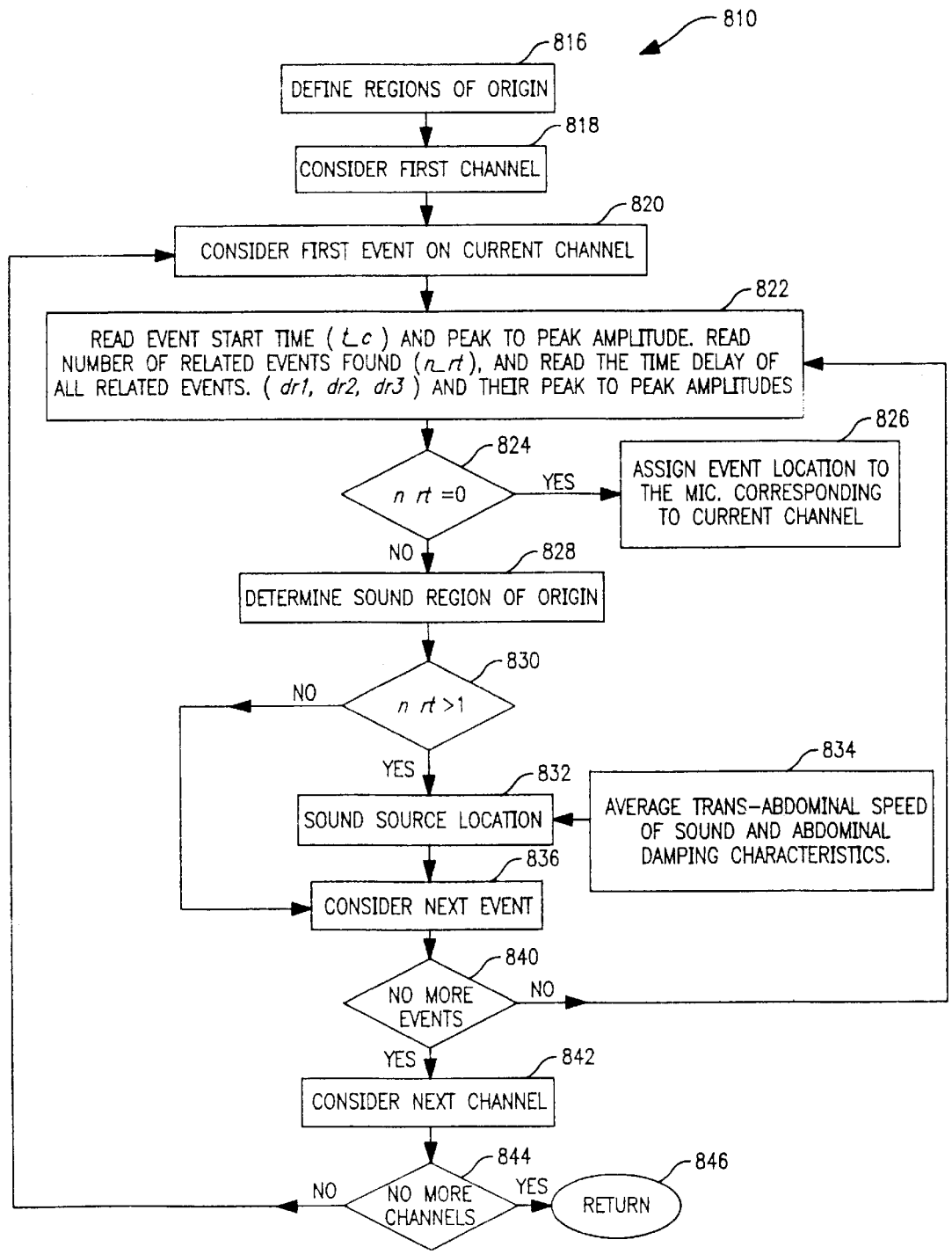
FIG. 30 is a flow diagram for localizing each of the gastrointestinal events.

In order to localize each event, the steps set forth in FIG. 30 are carried out.

Figure 31:
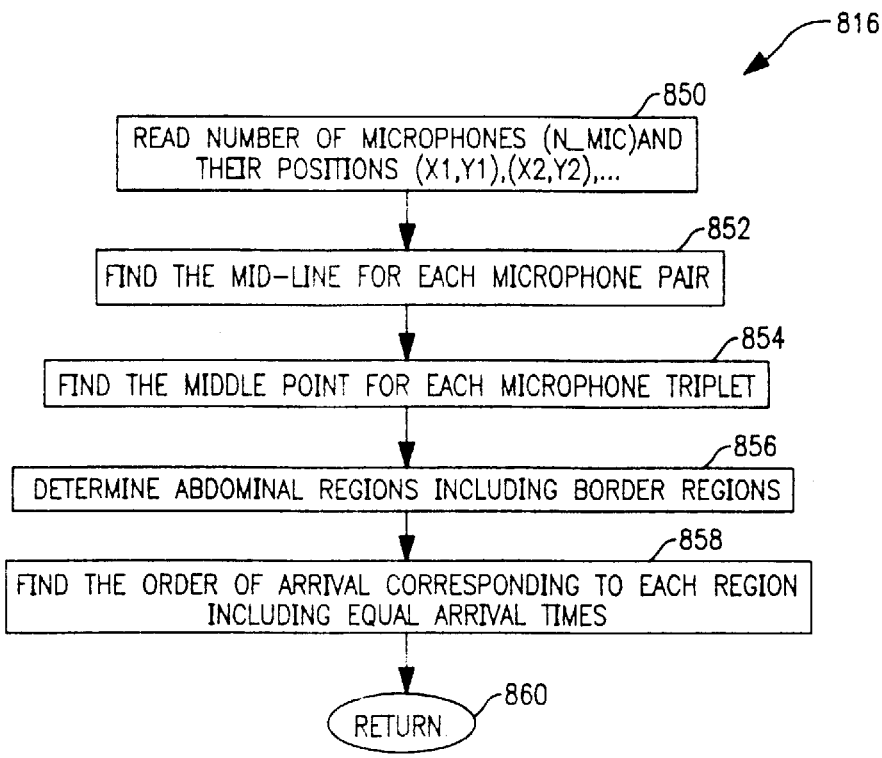
FIG. 31 is a flow diagram for defining sound regions of origin.

In order to perform the step 810 as shown in FIG. 30, the regions of origin are defined in the step 816, which is shown in more detail in FIG. 31. The first channel is then considered in a step 818 and the first event on the first channel is accessed in a step 820. The event start time and peak to peak amplitude are read and the number of related events and the time delay of the related events and the peak to peak amplitudes is also read. If the number of related events is equal to zero as tested for in step 824, the event location is assigned to the microphone corresponding to the current channel in step 826 and the event has been localized. In the event that the number of the related events is not equal to zero, the origin of the sound region is determined in a step 828 as is more fully set forth in FIG. 32.

A test is made in a step 830 to determine whether the number of related events is greater than one. If it is, the sound source location is determined in a step 832 as more fully set forth in FIG. 34. In addition, an input is received from a step 834 wherein the transabdominal speed of sound and abdominal damping characteristics have been determined as set forth in FIG. 33. Control is then transferred to the step 836, causing the next event to be considered. In a step 840 a test is made to determine whether there are any more events. If there are more events, control is transferred back to the step 822. If not, the next channel is considered in a step 842. A test is made in a step 834 to determine whether all channels have been processed. If they have not, the channel is incremented and control is transferred back to the step 820. If they have, the routine is exited in a step 846.

In order to define the regions of origin in step 816, the number of microphones and their positions are read in a step 850 as shown in FIG. 31. A midline is determined for each microphone pair in a step 852 and in a step 854 the middle point for each microphone triplet is determined. In a step 856, the abdominal regions are determined, including the border regions, and in a step 858 the order of arrival corresponding to each region, including equal arrival times, is determined following which the routine is exited in a step 860.

Figure 32:
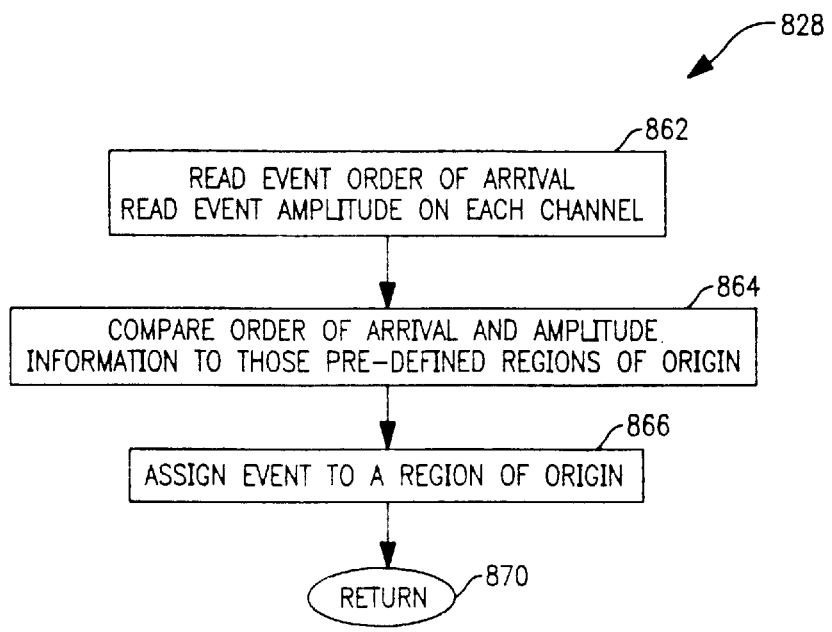
FIG. 32 is a flow diagram for determining a sound region of origin.
Figure 33:
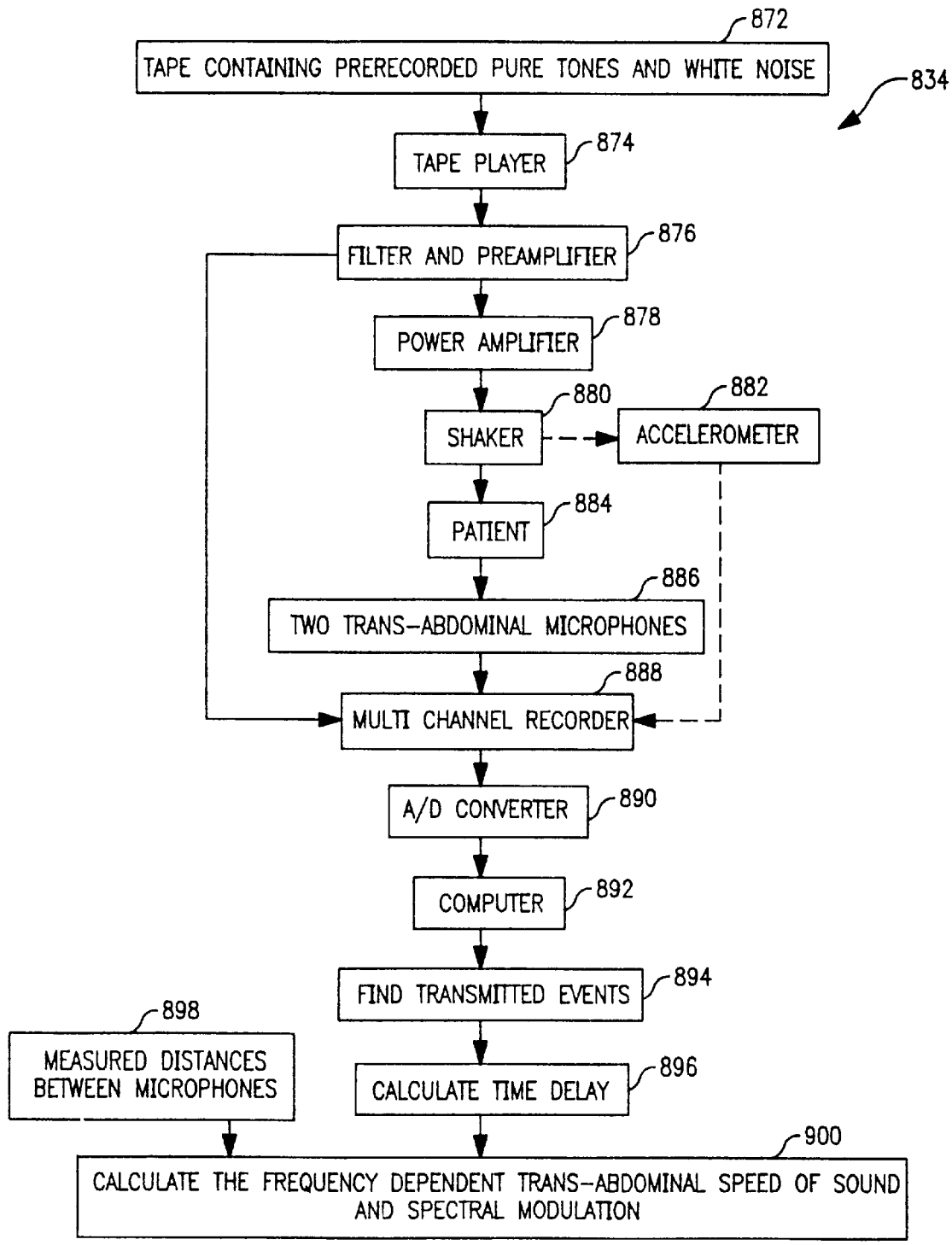
FIG. 33 is a flow diagram for determining the average transabdominal speed of sound and abdominal damping characteristics.

In order to determine the sound region of origin in step 828, in a step 862 the event order of arrival is read and the event amplitude on each channel is also read, as shown in FIG. 32. The order of arrival and amplitude information is compared to those of the predetermined regions of origin in a step 864. In a step 866 an event is assigned to a region of origin on the basis of the comparison and in a step 870 the routine is exited. In order to determine the average transabdominal speed and the abdominal damping characteristics in step 834, in a step 872 a tape containing prerecorded pure tones and white noise is played through a tape player in a step 874. That signal is fed through a filter and preamplifier in a step 876 and is boosted by a power amplifier in a step 878. A shaker coupled to an accelerometer in steps 880 and 882 provides vibration motion to a patient and a pair of transabdominal microphones in a step 886 pick up the resulting vibrational energy. That energy is recorded as electrical signals in a step 888 in a multichannel recorder and is converted in an analog to digital converter in a step 890 and stored in a computer in step 892. Transmitted signals and events are found in a step 894 and a time delay is calculated in a step 896. The time delay is fed in a step 900 to calculate the frequency dependent transabdominal speed of sound and spectral modulation and step 900 also receives the measured distances between the microphones from a step 898.

Figure 34:
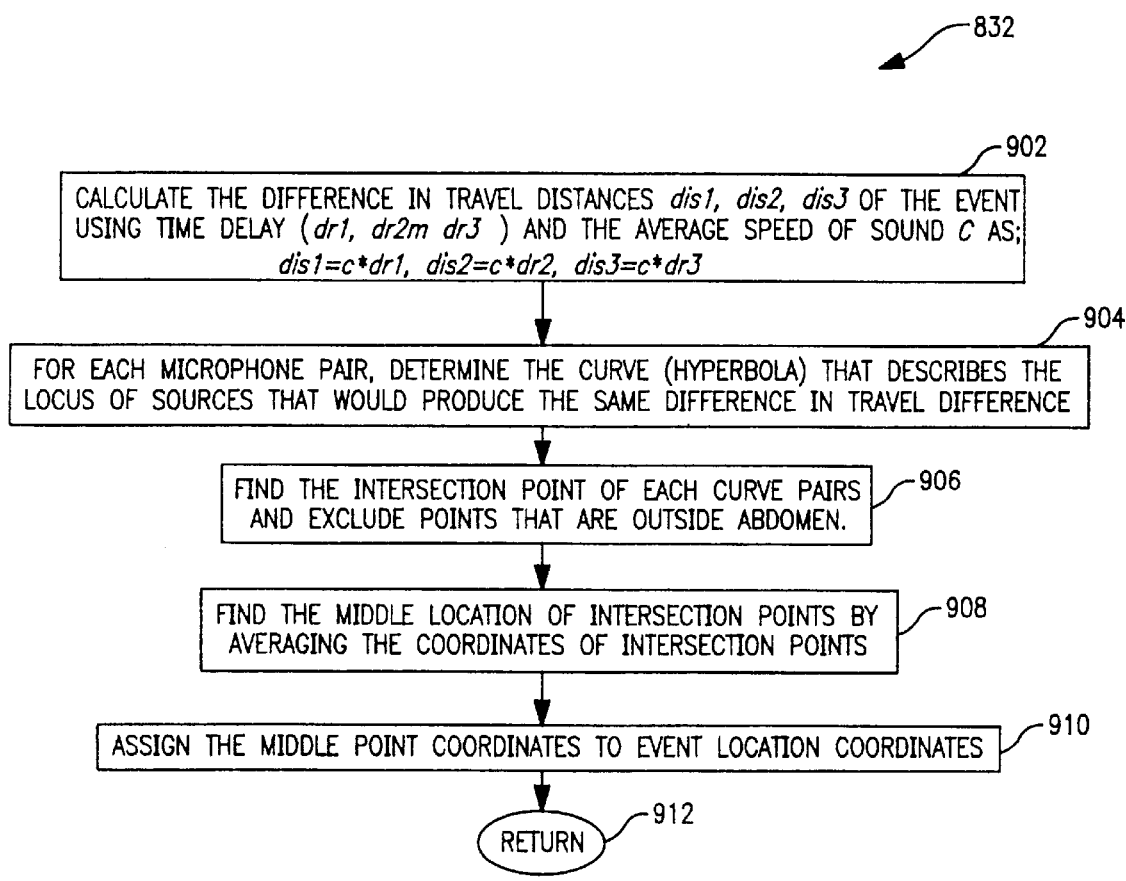
FIG. 34 is a flow diagram for determining a location of a sound source.

In order to determine the sound source location after learning the transabdominal speed and abdominal damping characteristics in a step 902 as shown in FIG. 34 the difference in travel distances of the events are calculated on the basis of the time delay and the average speed of sound obtained from step 834. In a step 904, for each microphone pair a hyperbolic curve is determined that describes the locus of sources that would produce the same difference in the sound travel differences. In a step 906 an intersection point of each of the curve pairs is determined and any points that are located outside the abdominal region are excluded from consideration. In a step 908 the middle location of intersection points is determined by averaging their coordinates. In a step 901 the middle point coordinates are assigned to event location coordinates and the routine is exited in a step 912.

Figure 35:
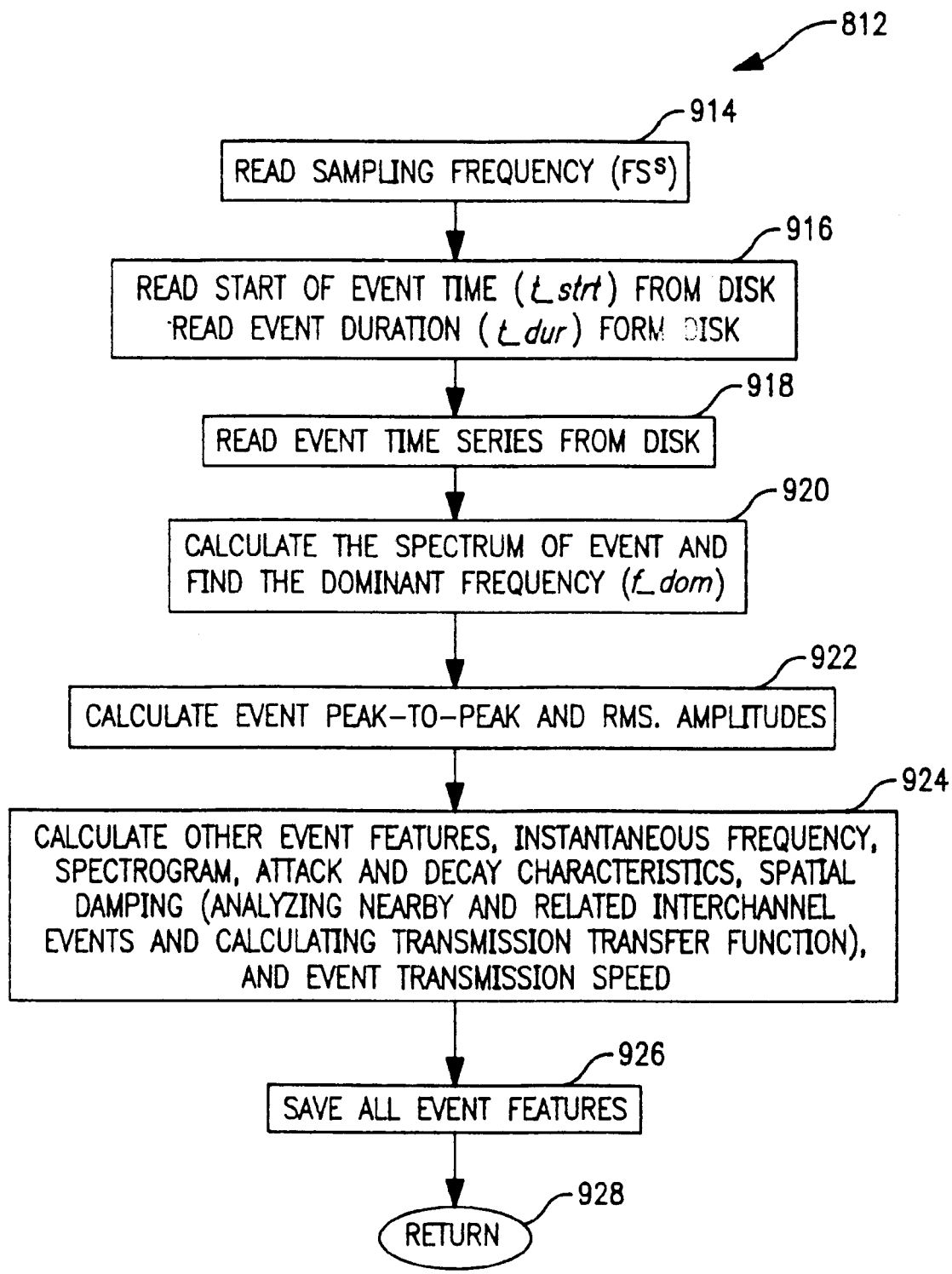
FIG. 35 is a flow diagram for combining event features.

In order to combine the event features as set forth in step 812, the sampling frequency is read in step 914 as shown in FIG. 35. The start of the event time is read from disk as is the event duration in a step 916. The event time series is then read from disk in a step 918, and the spectrum of the event and its dominant frequency are determined in a step 920. The peak to peak amplitudes and root-mean-square amplitudes of the event are calculated in a step 922. In a step 924 other event features, including the instantaneous frequency, spectrogram; attack and decay characteristics, spatial event damping and the like are determined from the amplitude envelope and spectrum of the event and from analyzing nearby and related interchannel events and calculating a transmission transfer function. The event transmission speed is also determined. These event features are saved in a step 926 and the routine is exited in a step 928.

Figure 36:
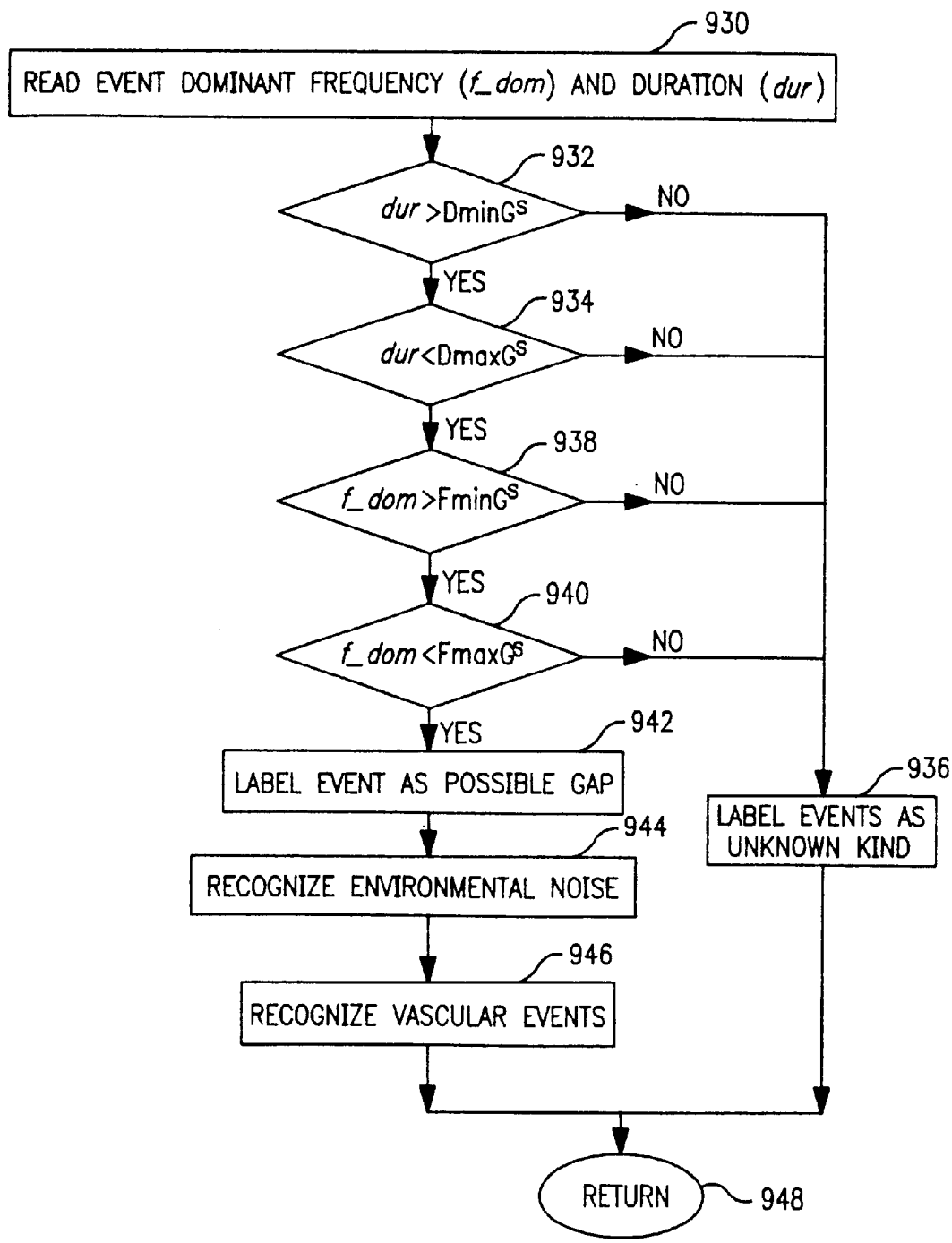
FIG. 36 is a flow diagram for recognizing gastrointestinal events.
Figure 37:
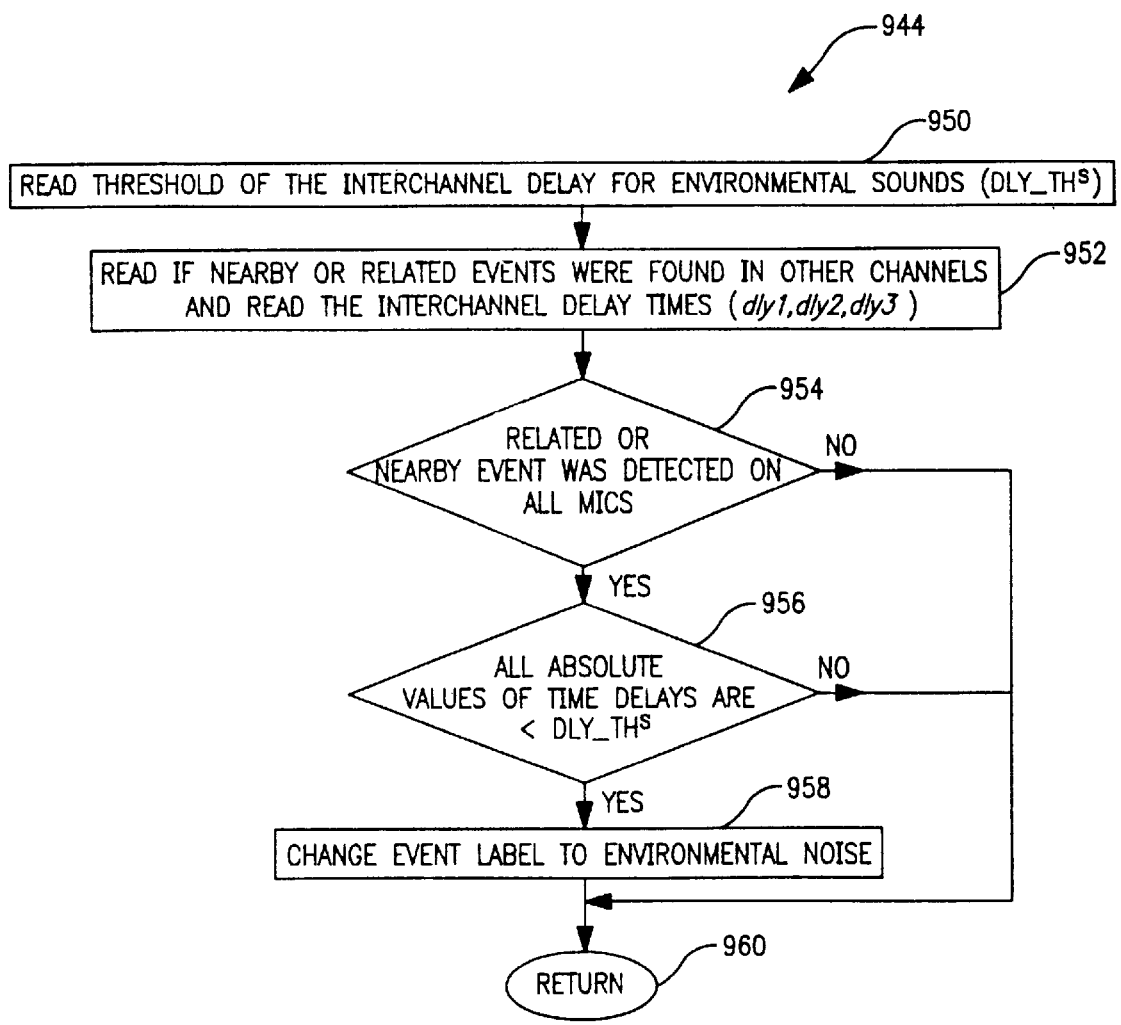
FIG. 37 is a flow diagram for recognizing environmental events of the type picked up by the free microphone.

Recognition of GAP events is carried out in the routine shown in FIG. 36. The event dominant frequency and duration are read in a step 930 and a test is made to determine whether the duration is greater than the minimum. If it is, control is transferred to a step 936 to determine whether the duration is less than the maximum. If it is, determinations are made in steps 938 and 940 to determine whether the dominant frequency is within a predetermined frequency range. In the event none of those tests hold true, control is transferred to a step 936 and the event is labeled as of an unknown kind. In the event that the duration of frequency range is within the windowed limitations, the event is labeled as a possible gastroacoustic phenomenon in step 942. A test is made in a step 944 to determine whether environmental noise, for instance, from the fourth channel, may have masked GAP event and a test is made in a step 946 to recognize vascular events. The routine is then exited in step 948. In order to perform step 944 to recognize environmental noise or events, the threshold of the interchannel delay for environmental sounds is read in a step 950, as shown in FIG. 37. A reading is made to determine if nearby or related labeled events were found in other channels and their interchannel delay times are read in step 952. In a step 954, a test is made to determine whether such a related or nearby event was detected on all microphones. If it was not, control is transferred to the return step 960. If it was, a test is made to determine whether the absolute value of the time delays is less than the interchannel delay for environmental sounds. If not, the routine is exited. If it is, the event label is changed to being one of environmental noise in a step 958.

Figure 38:
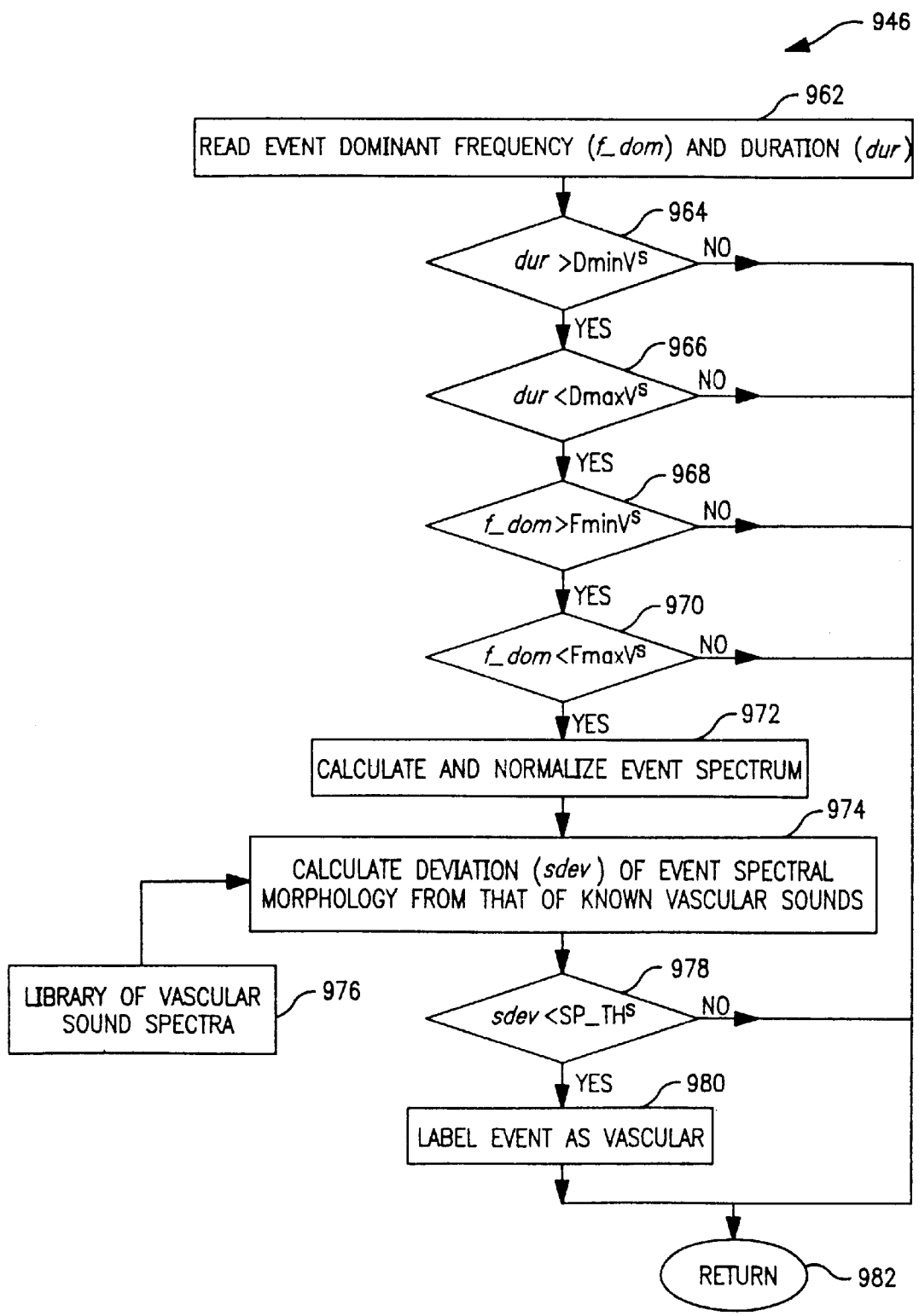
FIG. 38 is a flow diagram for recognizing signals representative of vascular events.

Vascular events are recognized in step 946, as set forth in FIG. 38. In a step 962, the dominant frequency and duration of the event are read and a test is made to determine whether the duration and the dominant frequency are within window values in steps 964 through 970. If they are not, control is transferred to the return step 982. If they are, an event spectrum is calculated in a step 972 and normalized. In a step 976, a series of data related to a library of vascular sound spectra are fed to a step 974 which receives the event spectrum and calculates the deviation of the event spectrum morphology from that of known vascular sounds. If the deviation is less than a spectral threshold value as tested for in step 978, the routine is exited. If the deviation is greater than or equal to the spectral threshold, the event is labeled as vascular in step 980 and the event is exited.

Figure 39:
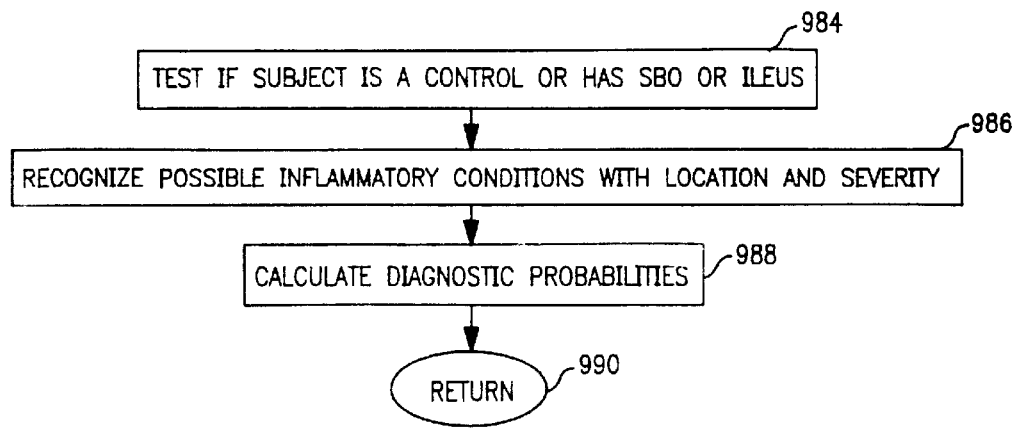
FIG. 39 is a pattern recognition flow diagram.
Figure 40:
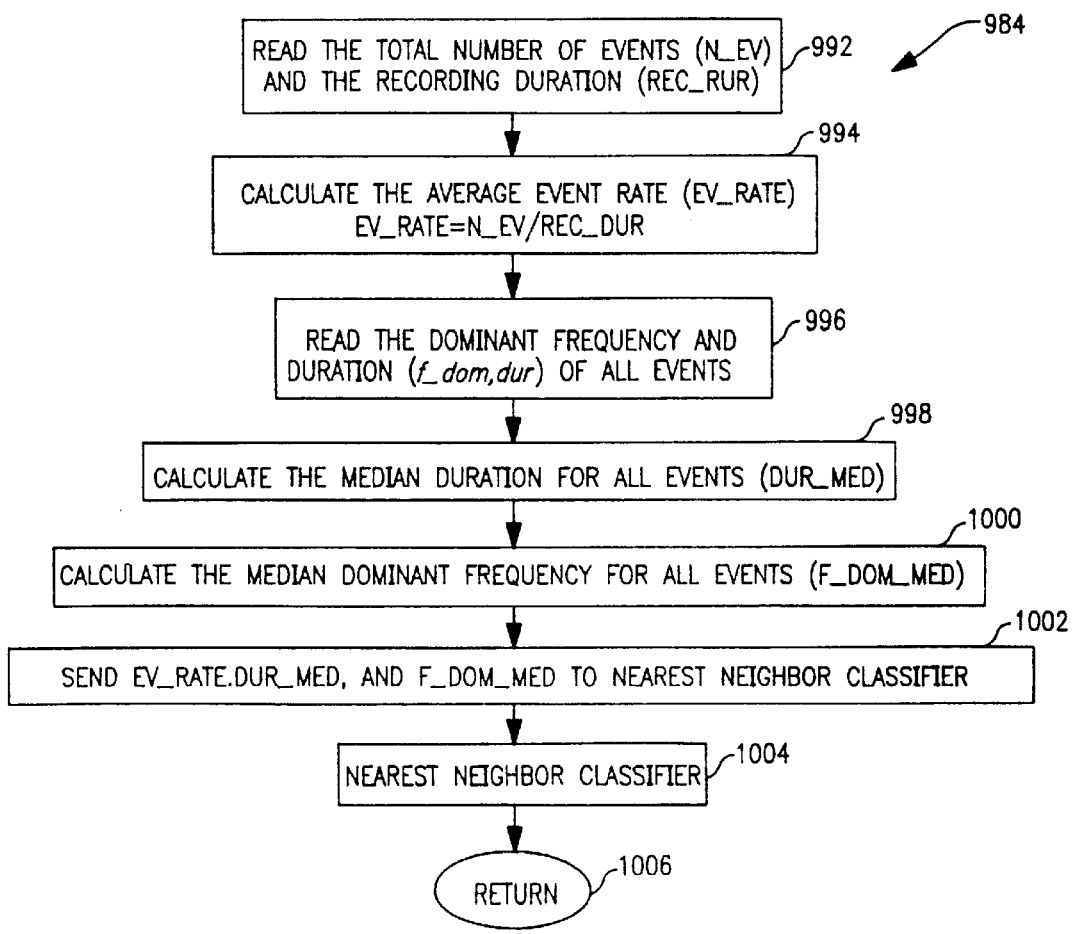
FIG. 40 is a flow diagram to test whether a subject is a control, has small bowel obstruction or ileus.
Figure 41:
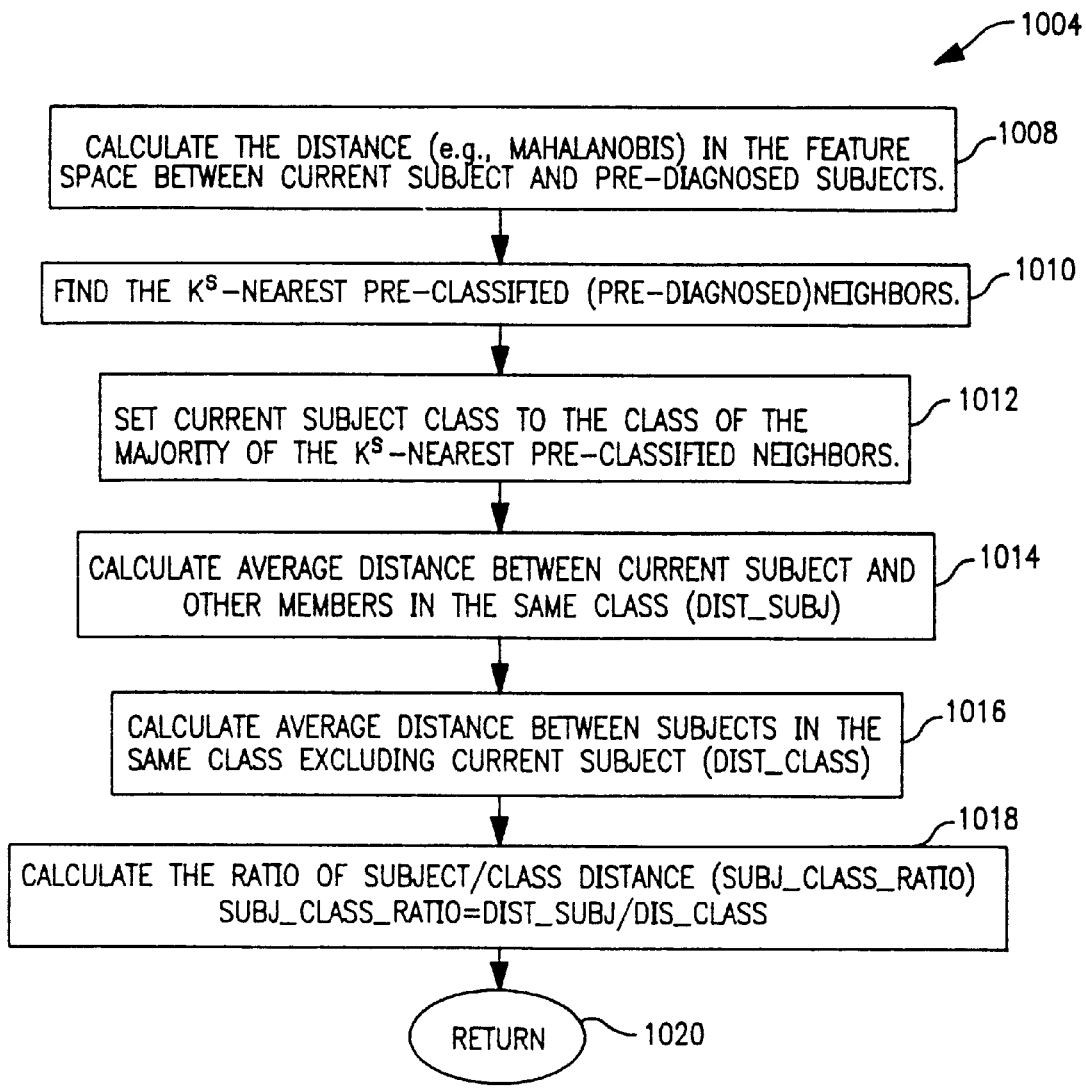
FIG. 41 is a flow diagram for nearest neighbor classification.

The system is also capable of performing pattern recognition and as set forth in FIG. 39, a test is made in a step 984 to determine if the patient or subject is a control or has small bowel obstruction or has ileus, as set forth in greater detail in FIG. 40. In a step 986, a test is made to determine whether the variables indicate possible inflammatory conditions with location and severity and in a step 988, diagnostic or probabilities are calculated and output and the routine is exited in a step 990.

The step 984 is carried out as shown in FIG. 40. In a step 992 the total number of events and the recording duration is read. In a step 994 the average event rate based on the previous value is determined and the dominant frequency and duration of all events is read in a step 996. The median duration for all events is calculated in step 998, and the median dominant frequency for all of the events is calculated in a step 1000. A nearest neighbor classifier receives the average event rate median duration and median dominant frequency and operates on values in a step 1004, as set forth in further detail in FIG. 41. The routine is then exited in step 1006.

In order to perform the nearest neighbor classification, the distance in the feature space is calculated between the current subject and prediagnosed subjects in a step 1008. The nearest preclassified or prediagnosed neighbors are determined in a step 1010 and the current subject class is set to the class of the majority of nearest neighbor preclassified neighbors in a step 1012. The average distance between a current subject and other members of the same class is determined within the space in a step 1014 and the average distance between the subjects in the same class, excluding the current subject is determined in a step 1016. The ratio of the subject class distance is then determined in the step 1018 and returned to the step 1020 exiting.

Figure 42:
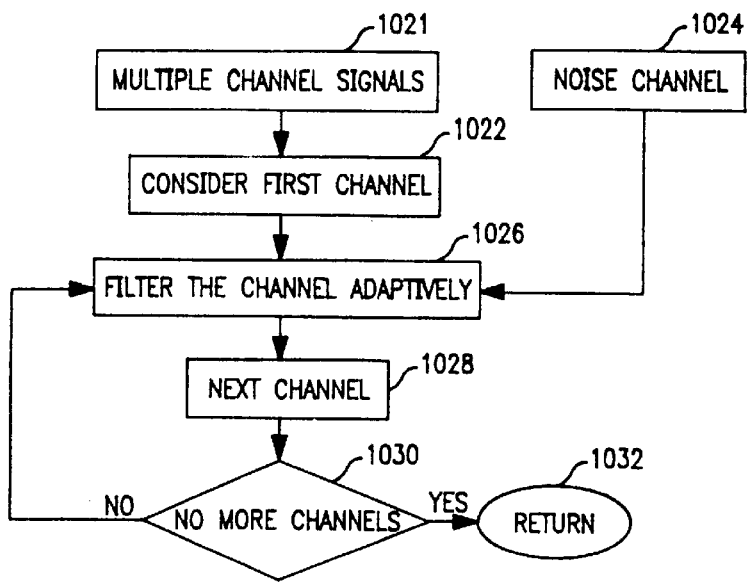
FIG. 42 is a flow chart of a method of adaptively filtering a channel signal.

Referring now to FIG. 42, a procedure is generally shown therein which may be executed at the microprocessor for filtering multiple channels when a noise estimate is received from a noise channel. In a step 1021, multiple channel signals are accessed and the first channel is accessed in a step 1022. A noise channel signal is accessed in a step 1024 and the channel selected is filtered adaptively in a step 1026. The next channel in the step 1028 and the test is done in the step 1030 to determine whether any more channels are available. If more channels are available, step 1026 is returned to. If not, the routine is exited.

Figure 43:
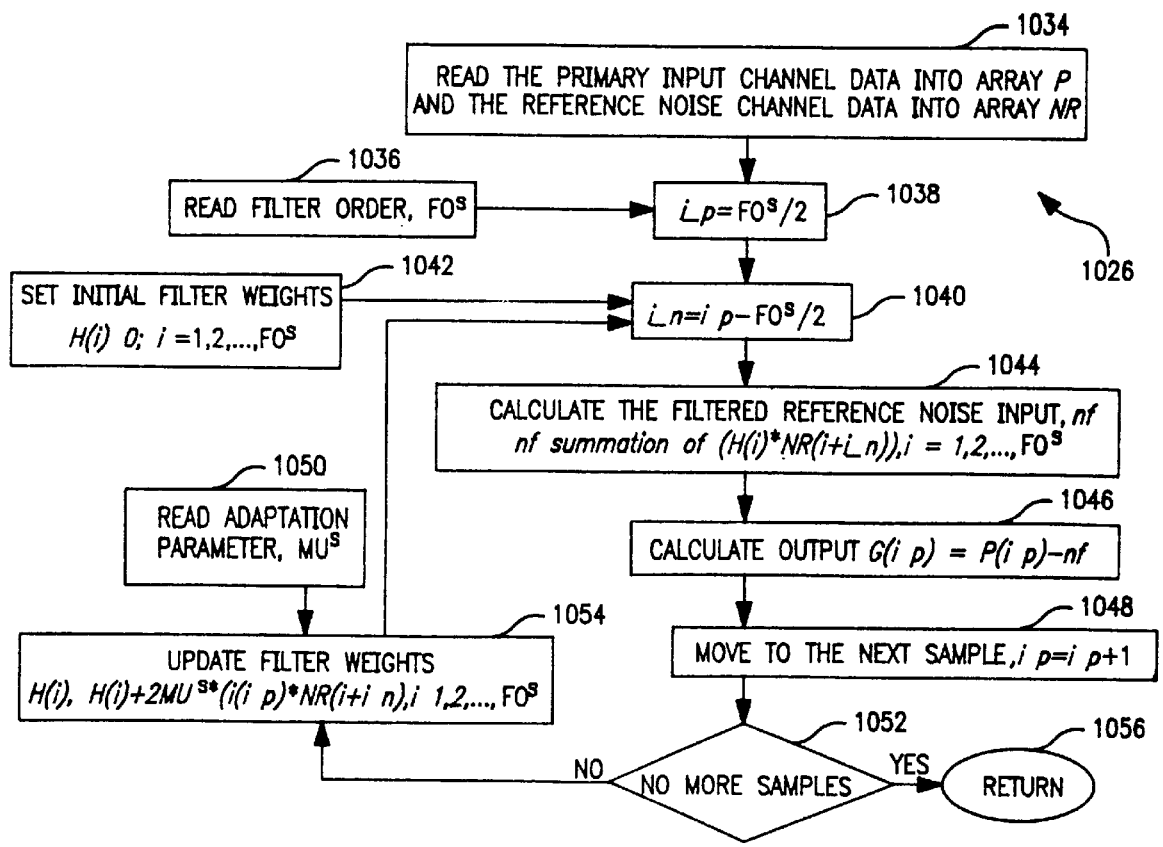
FIG. 43 is a flow chart of specific channel filtering steps of the process shown in FIG. 42.

The step 1026 is shown in further detail in FIG. 43, wherein in a step 1034 the primary input channel data is stored in an array P and the reference noise channel data from step 1024 is stored into an array NR. The filter order which has been preselected is read in a step 1036 and is divided by two in a step 1038 to provide i_p.

In a step 1040 the initial filter weights which were set to zero in step 1042 are inputted as is any update filter weights from step 1024 which may have been affected by an adaptation parameter $\mu$. All are provided to step 1040 where in i_n is determined as the difference between i_p and half of the filter order. The initial filter weights in the updated filter weights, however, are available at step 1040 but are not used in the calculation. In a step 1044 the filtered noise referenced input nf is calculated as the sum of the vector product of the initial or updated filter weights multiplied by the reference noise channel data. An output is calculated in step 1046 related to the difference between the primary input channel data and the reference noise input at that point. In a step 1048 the process is indexed to the next sample and a test is done in a step 1052 to determine whether there are more samples. If there are more samples, the filter weights are updated in a step 1054 on the basis of an adaptation parameter MU, which is doubled and then multiplied by the G output and the noise channel data array. The MU value is preset and the entire quantity is added to the previous filter weights to provide updated filter weights available at step 1040 for calculation of the filtered noise reference input in step 1044.

Figure 44:
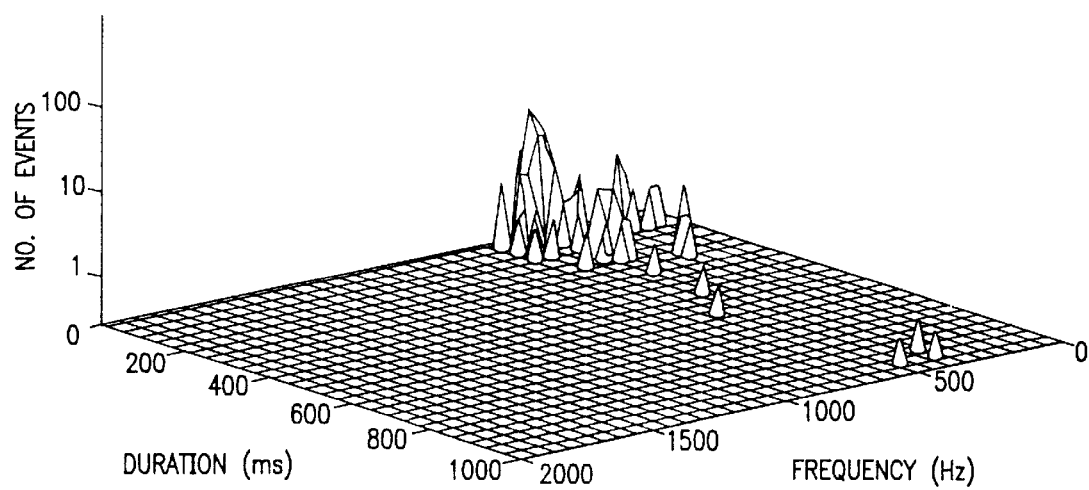
FIG. 44 is a plot of the number of events versus frequency versus duration from the epigastraeum of a normal subject.
Figure 45:
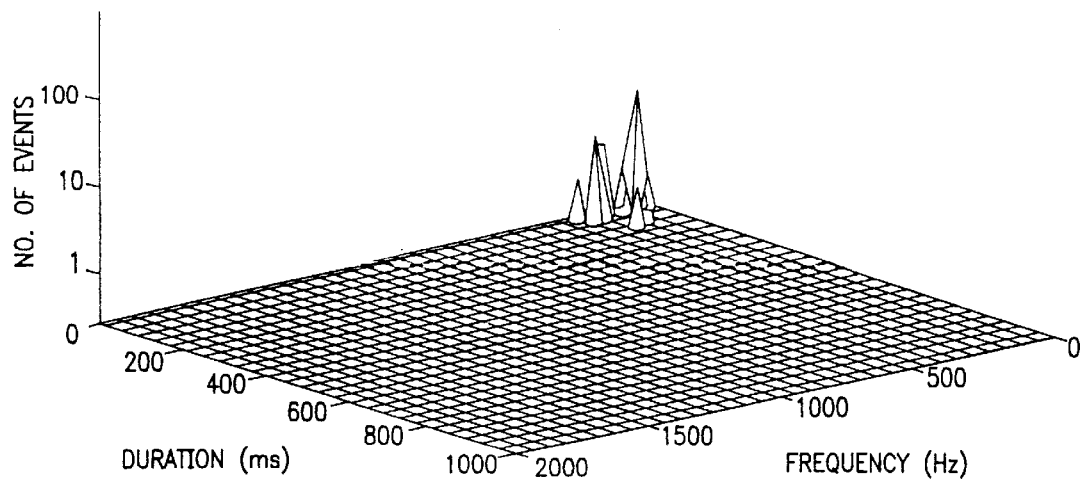
FIG. 45 is a plot of the lower quadrant of a subject with ileus.
Figure 46:
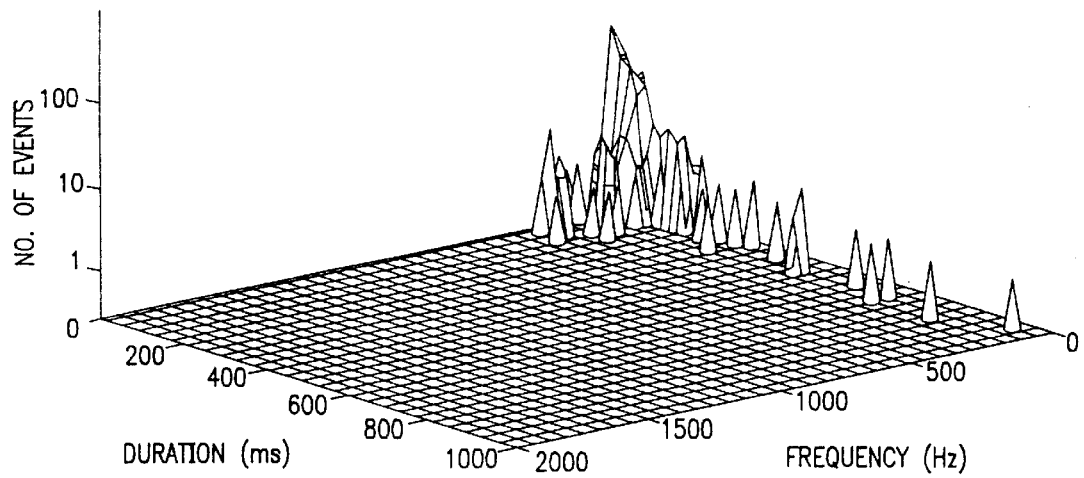
FIG. 46 is a plot of a subject with small bowel obstruction.

The system provided outputs in, among other forms, pseudo three-dimensional plots of acoustic frequency event duration and the number of events. For instance, as shown in FIG. 44, there is a clustering of GAP events with a given duration and dominant frequency. These GAP events were detected from the epigastraeum of a normal subject. It should be appreciated that the epigastraeum can have long duration events. A subject with ileus had a relatively small number of events and did not have long duration low frequency events as is shown in FIG. 45. GAP events collected from the right lower quadrant of a patient with small bowel obstruction showed a generally downward shifting of dominant frequencies plus very low frequency events in the near right hand corner of the plot as shown in FIG. 44. Tehse were not seen in normal patients or patients having ileus, as shown in FIG. 46.

Figure 47:
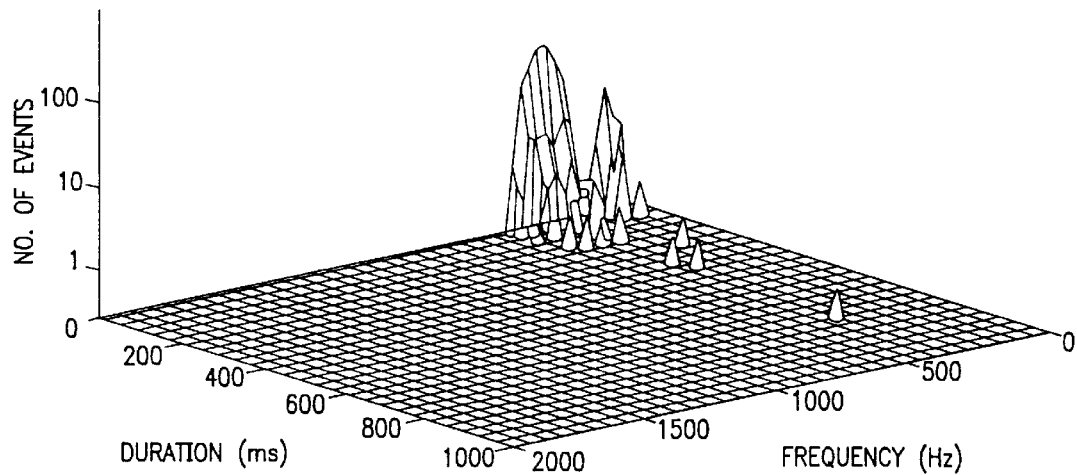
FIG. 47 is a plot from the lower right quadrant of a normal subject.
Figure 48:
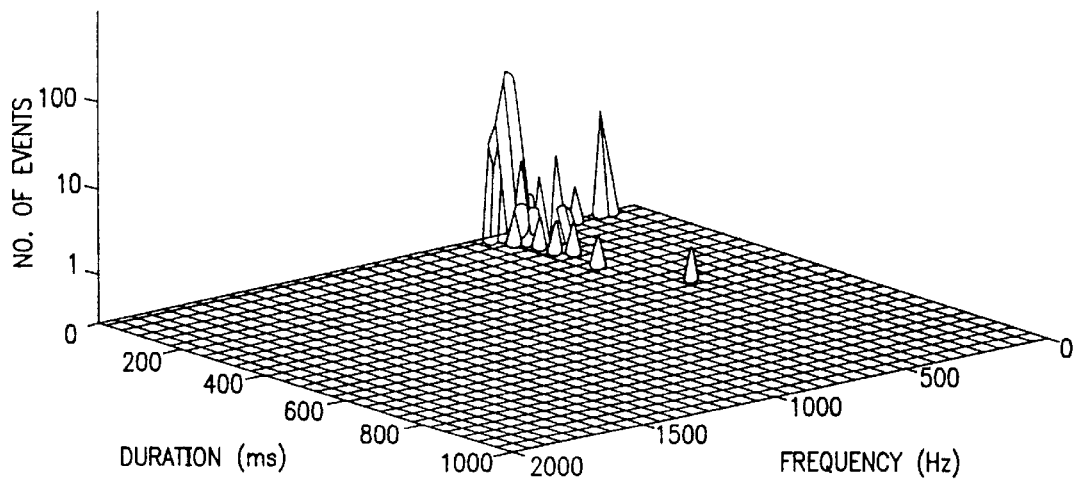
FIG. 48 is a plot from the lower left quadrant of a normal subject.
Figure 49:
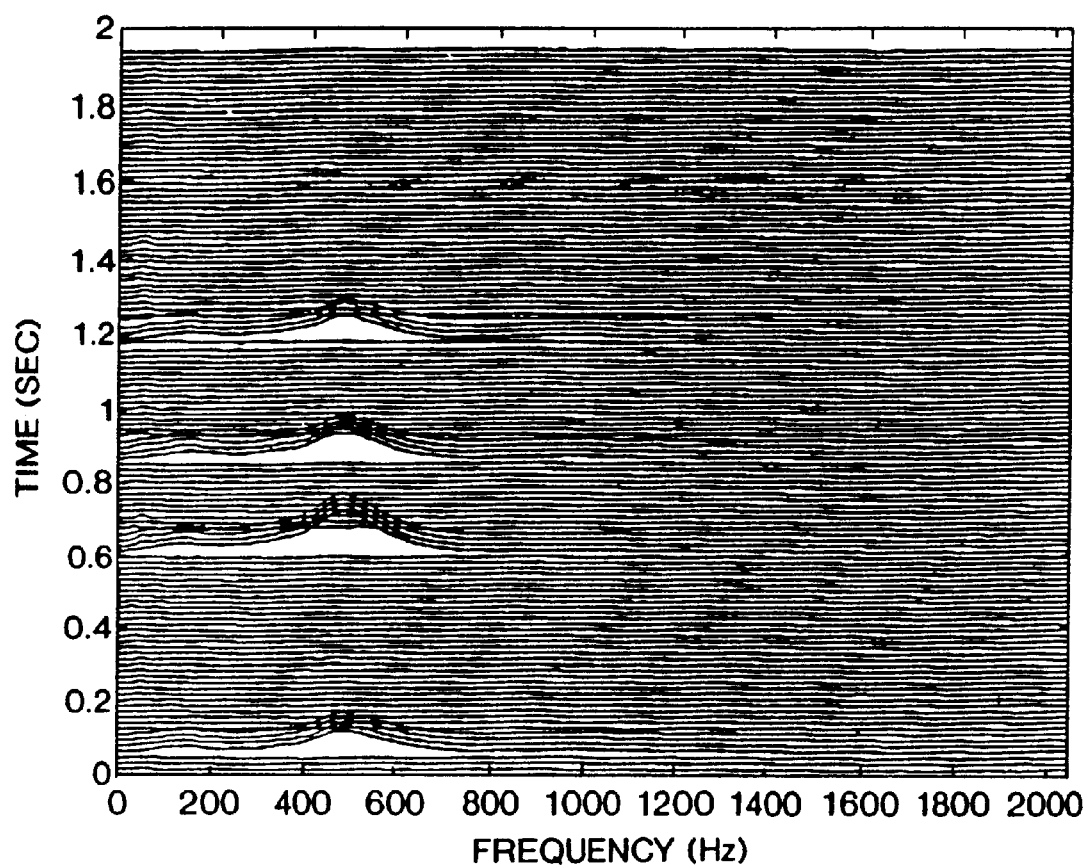
FIG. 49 is a spectrogram of four events in a normal subject.
Figure 50:
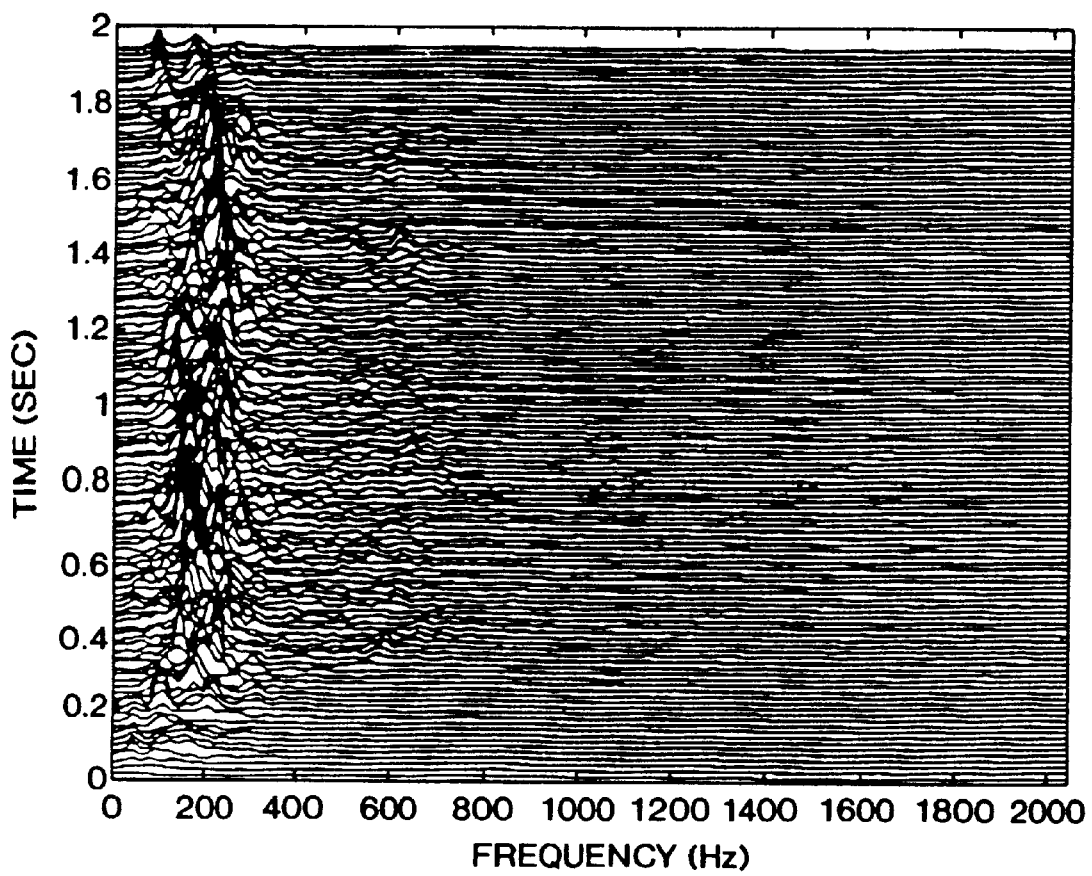
FIG. 50 is an event in a subject with small bowel obstruction.

In FIG. 47, a pseudo three-dimensional plot is shown of events from the right lower quadrant of a normal subject. The events are characterized by the absence of long duration and low frequency events. In FIG. 48 events taken from the left lower quadrant of a normal subject are similar in characteristic to those shown in FIG. 47. In FIG. 49 a spectrogram is shown of four events from a normal subject. The events are short and have a dominant frequency at about 500 Hz. In FIG. 50 a spectrogram is shown of a subject with small bowel obstruction which is characterized by long event duration and lowering of the dominant frequencies.

The bowel sound computerized analysis was performed in the diagnosis of human mechanical small bowel obstruction (SBO) after preliminary studies suggested diagnostic gastrointestinal acoustic phenomena (GAP) changes in a rat SBO model.

Fifty-three 20-minute GAP recordings were performed in 43 human subjects [37±18 (mean±SEM) years of age, range 2–94] using a four-microphone array. Recordings were digitized, and each GAP event analyzed for spectrum and duration. Follow-up was obtained on all patients, who were assigned to 1 of 5 categories: proven SBO by laparotomy or contrast radiography (5); suspected but unproved SBO (3); suspected but unproved ileus (3); definite ileus (7); and normal fasted controls (25).

The 8 proven and suspected SBO patients had similar findings, demonstrating major consistent differences from the 10 proven and suspected ileus subjects, and both these groups had significant differences from normal controls.

|  | SBO | Ileus | Control | Significant ($p < .05$) | | |
|---|---|---|---|---|---|---|
| n | 8 | 10 | 25 | yes | yes | yes |
| Number Events/min | 50 (29–60) | 5 (1.6–10) | 25 (7–46) | yes | yes | yes |
| Frequency (in Hz) | 210 (192–285) | 235 (213–280) | 325 (248–454) | no | yes | yes |
| Duration (in ms) | 34 (32–35) | 34 (32–35) | 31 (30–33) | no | no | no |

Values are median (25th–75th %). p values are for SBO-Ileus (S-I), SBO-Control (S-C), and Ileus-Control (I-C).

Beyond the median data, every obstructed patient but no non-obstructed subject demonstrated intermittent very long duration (1054±188 ms) and low frequency (168±62 Hz) events (>0.0001). Computerized bowel sound analysis may provide a noninvasive method to rapidly and safely diagnose mechanical bowel obstruction and differentiate it from ileus.

The auscultory finding of "high pitched rushes" with SBO may in fact be "low pitched rushes."

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

What is claimed is:

1. Apparatus for producing an output indication of a characteristic of a gastrointestinal sound comprising:

means for converting a gastrointestinal sound to a gastrointestinal signal;

means responsive to the gastrointestinal signal for producing a digitized gastrointestinal signal;

means responsive to the digitized gastrointestinal signal for determining a time of a gastrointestinal event;

means responsive to the digitized gastrointestinal signal for determining a spatial location of the gastrointestinal event; and means for determining a decay characteristic of the gastrointestinal event.

2. Apparatus for detecting and characterizing a gastrointestinal acoustical event comprising:

a transducer for converting a gastrointestinal sound to a gastrointestinal signal:

a converter for converting the gastrointestinal signal to a digitized gastrointestinal signal;

a gastrointestinal event-time marker generator responsive to the digitized gastrointestinal signal for providing a time marker associated with a gastrointestinal event;

a gastrointestinal event spatial location identifier responsive to the digitized gastrointestinal signal for identifying the location within a patient's body of the gastrointestinal event; and a decay characteristic detector for determining a decay characteristic of the digitized gastrointestinal signal.

3. A method for producing an output indication of a characteristic of a gastrointestinal sound comprising:

converting a gastrointestinal sound to a gastrointestinal signal;

producing a digitized gastrointestinal signal;

determining a time at which gastrointestinal event occurs;

determining a spatial position at which the gastrointestinal event occurs; and determining a decay characteristic of the gastrointestinal event.

* * * * *